US009534050B2

(12) United States Patent
Borghaei et al.

(10) Patent No.: US 9,534,050 B2
(45) Date of Patent: *Jan. 3, 2017

(54) ANTIBODIES TO TUMOR ENDOTHELIAL MARKER 7R

(71) Applicant: Institute for Cancer Research, Philadelphia, PA (US)

(72) Inventors: Hossein Borghaei, King of Prussia, PA (US); Louis M. Weiner, Washington, DC (US)

(73) Assignee: Institute for Cancer Research, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/514,493

(22) Filed: Oct. 15, 2014

(65) Prior Publication Data

US 2015/0064190 A1 Mar. 5, 2015

Related U.S. Application Data

(63) Continuation of application No. 13/697,024, filed as application No. PCT/US2011/036124 on May 11, 2011, now Pat. No. 8,883,978.

(60) Provisional application No. 61/333,554, filed on May 11, 2010.

(51) Int. Cl.
| C07K 16/28 | (2006.01) |
| A61K 51/10 | (2006.01) |
| C07K 16/30 | (2006.01) |
| A61K 47/48 | (2006.01) |
| A61K 39/00 | (2006.01) |

(52) U.S. Cl.
CPC ......... *C07K 16/28* (2013.01); *A61K 47/48561* (2013.01); *A61K 51/1027* (2013.01); *A61K 51/1063* (2013.01); *C07K 16/3046* (2013.01); *A61K 2039/505* (2013.01); *C07K 2317/33* (2013.01); *C07K 2317/622* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 6,936,705 B1 | 8/2005 | Honjo et al. |
| 7,348,003 B2 | 3/2008 | Salcedo et al. |
| 2005/0287140 A1 | 12/2005 | Smothers et al. |
| 2006/0246506 A1 | 11/2006 | Pulli et al. |
| 2007/0196369 A1 | 8/2007 | Hoogenboom et al. |
| 2009/0017030 A1 | 1/2009 | St. Croix et al. |

FOREIGN PATENT DOCUMENTS

WO 2008/153237 12/2008

OTHER PUBLICATIONS

Rudikoff et al. (Proc. Natl. Acad. Sci. USA, 79(6): 1979-1983, 1982).*
McCarthy et al. (J. Immunol. Methods, 251(1-2): 137-149, 2001).*
McCarthy et al. (Journal of Immunological Methods, 251: 137-149, 2001).*
Jackson et al. (J. Immunol., 154:3310-3319, 1995).*
Adams, G. P., et al., "Highly Specific in Vivo Tumor Targeting by Monovalent and Divalent Forms of 741F8 Anti-c-erbB2 Single-Chain Fv", Cancer Research 53, 4026-4034, Sep. 1, 1993.
Adams, G. P., et al., "Increased Affinity Leads to Improved Selective Tumor Delivery of Single-Chain Fv Antibodies", Cancer Research 58, 485-490, Feb. 1, 1998.
Adams, G.P., et al., "Generating improved single-chain Fv molecules for tumor targeting", J. Immunol. Methods, Dec. 10, 1999, 231(1-2):249-60.
Carson-Walter, E.B., et al., "Cell Surface Tumor Endothelial Markers are Conserved in Mice and Humans", Cancer Research 61, 6649-6655, Sep. 15, 2001.
Gussow, et al., "Humanization of Monoclonal Antibodies", Methods Enzymol., 1991; 203:99-121.
Imgenex, "Monoclonal Antibody to Tumor Endothelial Marker 7 (TEM7)"; Nov. 9, 2004.
International Search Report and Written Opinion dated Aug. 9, 2011 issued in counterpart International Application No. PCT/US11/36124.
Kingsbury, G. A., et al., "Screening of phage display immunoglobulin libraries by anti-M13 ELISA and whole phage PCR", Nucleic Acids Research, 1995, vol. 23, No. 13, 2563-2564.
Mariuzza, et al., "The Structural Basis of Antigen-Antibody Recognition", Annu. Rev. Biophys. Biophys. Chem., 1987; 16:139-59.
Marks, J.D., et al., "By-passing immunization. Human antibodies from V-gene libraries displayed on phage", J. Mol. Biol., Dec. 5, 1991, 222(3):581-97.
Nanda et al., "Identification of a Binding Partner for the Endothelial Cell Surface Proteins TEM7 and TEM7R", Cancer Research, Dec. 1, 2004, vol. 64, No. 23, pp. 8507-8511.
Robinson, M.K., et al., "Quantitative Immuno-Positron Emission Tomography Imaging of HER2-Positive Tumor Xenografts with an Iodine-124 Labeled Anti-HER2 Diabody", Cancer Research 2005, 65:(4)1471-1478, Feb. 15, 2005.
Schier, R., et al., "In vitro and in vivo characterization of human anti-c-erbB-2 single-chain Fv isolated from a filamentous phage antibody library", Immunotechnology, Mar. 1995, 1(1):73-81.
Schier, R., et al., "Isolation of picomolar affinity anti-c-erbB-2 single-chain Fv by molecular evolution of the complementarity determining regions in the center of the antibody binding site", J. Mol. Biol., Nov. 8, 1996, 263(4):551-67.

(Continued)

*Primary Examiner* — Misook Yu
*Assistant Examiner* — Nelson B Moseley, II
(74) *Attorney, Agent, or Firm* — Stradley Ronon Stevens & Young, LLP

(57) ABSTRACT

Antibodies that specifically bind to an epitope on the extracellular domain of TEM7R are provided. Nucleic acids encoding such antibodies and cells capable of expressing such antibodies are also provided. The antibodies may be used in methods for treating tumors and for inhibiting angiogenesis in tumors.

24 Claims, 25 Drawing Sheets

(56) References Cited

OTHER PUBLICATIONS

St. Croix, B., et al., "Genes expressed in human tumor endothelium", Science, Aug. 18, 2000, 289(5482):1197-202.
Stamatopoulos et al., "Immunoglobulin light chain repertoire in chronic lymphocytic leukemia"; Blood, Nov. 15, 2005, vol. 106, No. 10, pp. 3575-3583.
Winkler, et al., "Changing the Antigen Binding Specificity by Single Point Mutations of an Anti-p24 (HIV-1) Antibody", (J. Imm., 265;4505-4514, 2000).
Yuan, Q.A., et al., "Development of engineered antibodies specific for the Muellerian inhibiting substance type II receptor: a promising candidate for targeted therapy of ovarian cancer", Mol. Cancer Ther., Aug. 2006, 5(8):2096-105.
Rudnick et al., "Affinity and Avidity in Antibody-Based Tumor Targeting", Cancer Biother. Radiopharm., 2009, 24:155-61.
Barbas, et al., "In vitro Evolution of a Neutralizing Human Antibody to Human Immunodeficiency Virus Type 1 to Enhance Affinity and Broaden Strain Cross-Reactivity", Proc. Natl. Acad. Sci. USA, 1994, 91:3809-13.
Yang, et al., "CDR Walking Mutagenesis for teh Affinity Maturation of a Potent Human Anti-HIV-1 Antibody into the Picomolar Range", J. Mol. Biol., 1995, 254:392-403.
Ho, et al., "In vitro Antibody Affinity Maturation Targeting Germline Hotspots", Methods Mol. Biol., 2009, 525:293.
Yau, et al., "Affinity Maturation of a VHH by Mutational Hotspot Randomization", J. Immunol. Methods, 2005, 297:213-24.
Wark, et al., "Latest Technologies for the Enhancement of Antibody Affinity", Adv. Drug Delivery Rev., 2006, 58:657-670.
Lippow, et al., "Computational Design of Antibody-Affinity Improvement Beyond in vivo Maturation", Nat. Biotechnol., 2007, 25:1171-6.
Barderas, et al., Affinity Maturation of Antibodies Assisted by in silico Modeling, Proc. Natl. Acad. Sci. USA, 2008, 105:9029-34.
North, et al., "A New Clustering of Antibody CDR Loop Conformations", J. Mol. Biol., 2011, 406:228-256.
Schier, et al., "Isolation of Picomolar Affinity Anti-c-erbB2 Single-chain Fv by Molecular Evolution of the Complementarity Determining Regions in the Center of the Antibody Binding Site", J. Mol. Biol., 1996, 263:551-7.

\* cited by examiner

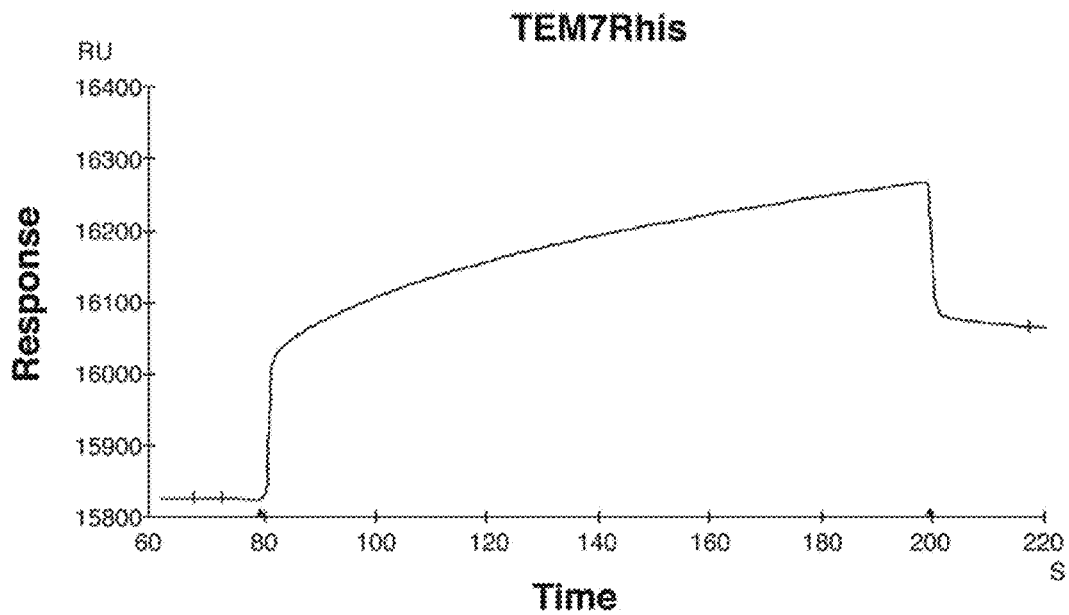

| Fc | APROG | Time | AbsResp | Slope | Baseline | RelResp | Id |
|---|---|---|---|---|---|---|---|
| 2 | kinetics | 70.5 | 15826.8 | 0.01 | Yes | 0 | BASELINE |
| 2 | kinetics | 220.5 | 16060.4 | -0.58 | No | 233.6 | TEM7Rhis |
| 2 | kinetics | 501.5 | 15849.0 | -0.05 | No | 22.2 | REGENERATION |

| Time | Info |
|---|---|
| 0.0 | Timestamp: 03-May-04 16:52:19 |
| 0.0 | Set Temperature: 25.0 °C |
| 0.0 | Temperature: 25.02 °C |
| 0.0 | Rack 1 (Left): THERMO_C |
| 0.0 | Rack 2 (Right): THERMO_A |
| 0.0 | Flow Cell: 2 |
| 0.0 | Flow: 50 µl/min |
| 0.0 | Data Collection: 1Hz |
| 79.1 | Inject: Start Fc 2 R2A1 |
| 199.7 | Inject: Ready 100 µl |
| 277.0 | Inject: Start Fc 2 R2F3 |
| 279.5 | Low Quality Data in Fc 2 |
| 280.5 | Low Quality Data in Fc 2 |
| 289.6 | Inject: Ready 10 µl |
| 290.5 | Low Quality Data in Fc 2 |
| 291.5 | Normal Quality Data in Fc 2 |
| 380.4 | Inject: Start Fc 2 R2F4 |
| 393.0 | Inject: Ready 10 µl |
| 478.9 | Flowfill: Start |
| 486.3 | Flowfill: Ready |
| 519.2 | Inject: Start Fc 2 R2F5 |
| 537.8 | Inject: Ready 15 µl |
| 559.5 | Temperature: 25.01 °C |

Fig. 1b

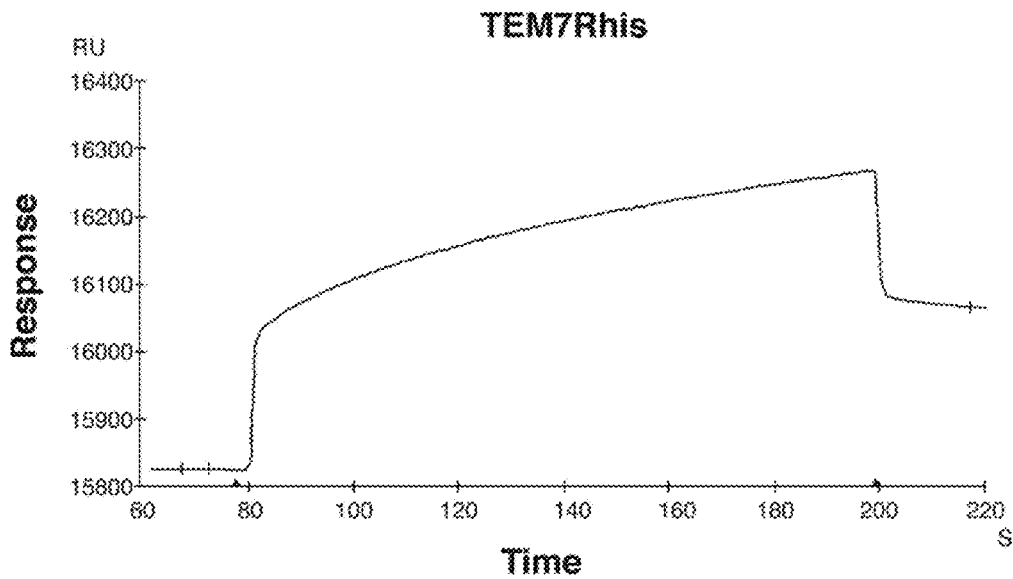

| Fc | APROG | Time | AbsResp | Slope | Baseline | RelResp | Id |
|---|---|---|---|---|---|---|---|
| 2 | kinetics | 70.5 | 15826.8 | 0.01 | Yes | 0 | BASELINE |
| 2 | kinetics | 220.5 | 16060.4 | -0.58 | No | 233.6 | TEM7Rhis |
| 2 | kinetics | 501.5 | 15849.0 | -0.05 | No | 22.2 | REGENERATION |

| Time | Info |
|---|---|
| 0.0 | Timestamp: 03-May-04 16:52:19 |
| 0.0 | Set Temperature: 25.0 °C |
| 0.0 | Temperature: 25.02 °C |
| 0.0 | Rack 1 (Left): THERMO_C |
| 0.0 | Rack 2 (Right): THERMO_A |
| 0.0 | Flow Cell: 2 |
| 0.0 | Flow: 50 µl/min |
| 0.0 | Data Collection: 1Hz |
| 79.1 | Inject: Start Fc 2 R2A1 |
| 199.7 | Inject: Ready 100 µl |
| 277.0 | Inject: Start Fc 2 R2F3 |
| 279.5 | Low Quality Data in Fc 2 |
| 280.5 | Low Quality Data in Fc 2 |
| 289.6 | Inject: Ready 10 µl |
| 290.5 | Low Quality Data in Fc 2 |
| 291.5 | Normal Quality Data in Fc 2 |
| 380.4 | Inject: Start Fc 2 R2F4 |
| 393.0 | Inject: Ready 10 µl |
| 478.9 | Flowfill: Start |
| 486.3 | Flowfill: Ready |
| 519.2 | Inject: Start Fc 2 R2F5 |
| 537.8 | Inject: Ready 15 µl |
| 559.5 | Temperature: 25.01 °C |

Fig. 1c

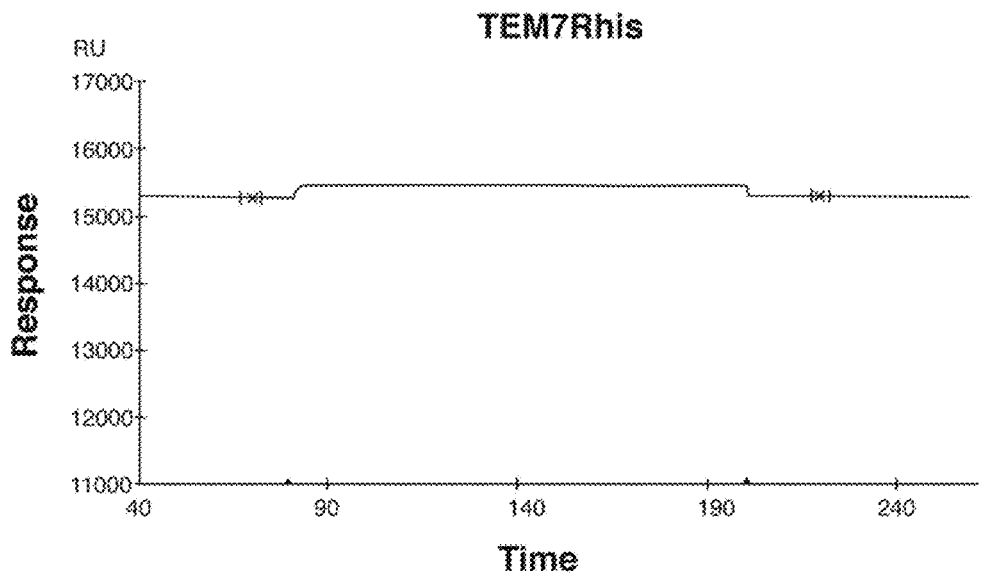

| Fc | APROG | Time | AbsResp | Slope | Baseline | RelResp | Id |
|---|---|---|---|---|---|---|---|
| 4 | kinetics | 70.5 | 15287.4 | 0.02 | Yes | 0 | BASELINE |
| 4 | kinetics | 220.5 | 15304.7 | 0.00 | No | 17.3 | TEM7Rhis |
| 4 | kinetics | 503.5 | 15294.0 | -0.06 | No | 6.6 | REGENERATION |

| Time | Info |
|---|---|
| 0.0 | Timestamp: 03-May-04 17:03:51 |
| 0.0 | Set Temperature: 25.0 °C |
| 0.0 | Temperature: 24.99 °C |
| 0.0 | Rack 1 (Left): THERMO_C |
| 0.0 | Rack 2 (Right): THERMO_A |
| 0.0 | Flow Cell: 4 |
| 0.0 | Flow: 50 µl/min |
| 0.0 | Data Collection: 1Hz |
| 79.8 | Inject: Start Fc 4 R2A1 |
| 200.5 | Inject: Ready 100 µl |
| 278.3 | Inject: Start Fc 4 R2F3 |
| 280.5 | Low Quality Data in Fc 4 |
| 290.9 | Inject: Ready 10 µl |
| 292.5 | Normal Quality Data in Fc 4 |
| 382.5 | Inject: Start Fc 4 R2F4 |
| 395.2 | Inject: Ready 10 µl |
| 482.2 | Flowfill: Start |
| 489.6 | Flowfill: Ready |
| 522.7 | Inject: Start Fc 4 R2F5 |
| 541.3 | Inject: Ready 15 µl |
| 563.5 | Temperature: 25.02 °C |

Fig. 1d

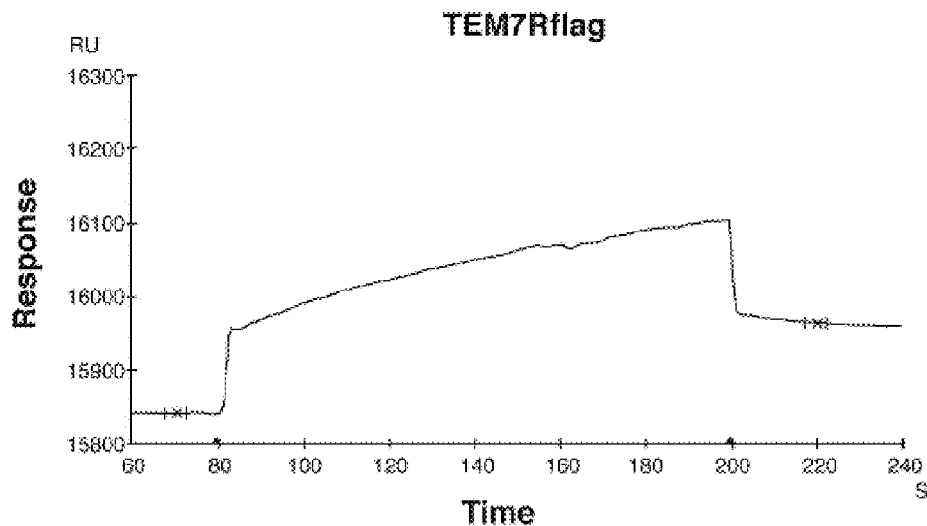

| Fc | APROG | Time | AbsResp | Slope | Baseline | RelResp | Id |
|---|---|---|---|---|---|---|---|
| 2 | kinetics | 70.5 | 15840.6 | 0.05 | Yes | 0 | BASELINE |
| 2 | kinetics | 220.5 | 15961.3 | -0.20 | No | 120.7 | TEM7Rflag |
| 2 | kinetics | 502.5 | 15847.9 | -0.05 | No | 7.3 | REGENERATION |

| Time | Info |
|---|---|
| 0.0 | Timestamp: 03-May-04 17:15:26 |
| 0.0 | Set Temperature: 25.0 °C |
| 0.0 | Temperature: 25.02 °C |
| 0.0 | Rack 1 (Left): THERMO_C |
| 0.0 | Rack 2 (Right): THERMO_A |
| 0.0 | Flow Cell: 2 |
| 0.0 | Flow: 50 µl/min |
| 0.0 | Data Collection: 1Hz |
| 79.2 | Inject: Start Fc 2 R2A1 |
| 199.8 | Inject: Ready 100 µl |
| 277.3 | Inject: Start Fc 2 R2F3 |
| 279.5 | Low Quality Data in Fc 2 |
| 280.5 | Low Quality Data in Fc 2 |
| 289.9 | Inject: Ready 10 µl |
| 290.5 | Low Quality Data in Fc 2 |
| 291.5 | Normal Quality Data in Fc 2 |
| 380.9 | Inject: Start Fc 2 R2F4 |
| 393.4 | Inject: Ready 10 µl |
| 479.4 | Flowfill: Start |
| 486.8 | Flowfill: Ready |
| 519.8 | Inject: Start Fc 2 R2F5 |
| 538.3 | Inject: Ready 15 µl |
| 559.5 | Temperature: 25.01 °C |

Fig. 1e

SEQUENCE LISTING

<160> NUMBER OF SEQ ID NOS: 19

<210> SEQ ID NO 1
<211> LENGTH: 18
<212> TYPE: DNA
<213> ORGANISM: artificial

```
<220> FEATURE:
<223> OTHER INFORMATION: Completely synthesized

<400> SEQUENCE: 1
gaaataccta ttgcctac                                                 18

<210> SEQ ID NO 2
<211> LENGTH: 19
<212> TYPE: DNA
<213> ORGANISM: artificial
<220> FEATURE:
<223> OTHER INFORMATION: completely synthesized

<400> SEQUENCE: 2
cttattagcg tttgccatt                                                19

<210> SEQ ID NO 3
<211> LENGTH: 790
<212> TYPE: DNA
<213> ORGANISM: Homo sapiens

<400> SEQUENCE: 3
cgcggcccag ccggccatgg cccaggtgca gctggtggag tctgggggag gcttggtaca    60
gcctgggggg tccctgagac tctcctgtgc agcctctgga ttcaccttca gtagttatga   120
aatgaactgg gtccgccagg ctccagggaa ggggctggag tgggtttcat acattagtag   180
tagtggtagt accatatact acgcagactc tgtgaagggc cgattcacca tctccagaga   240
caattccaag aacacgctgt atctgcaaat gaacagcctg agagctgagg acacggctgt   300
gtattactgt gcgagtgggg actatatgga cgtctgggggc caggggacca cggtcaccgt   360
ctcctcatcg gcctcggggg ccgaattggg cggcggcggc tccggaggag gaggatctgg   420
tggtggtggt tcgactagtg acatccagtt gacccagtct ccatcctccc tgtctgcatc   480
tgttggagac agagtcacca tcacttgcca ggcgagtcag acattagca actatttaaa   540 ttggtatcag cagaaaccag ggaaagcccc taagctcctg atgtacgatg catccaattt   600
ggaaacaggg gtcccatcaa ggttcagtgg aagtggatct gggacagatt ttactttcac   660
catcagcagc ctgcagcctg aagattttgc aacatattac tgtcaacagt ctgataatct   720
cccgtacact tttggccagg ggaccaaagt ggatatcaaa cgctcgagcc atcaccatca   780
tcaccattaa                                                         790

<210> SEQ ID NO 4
<211> LENGTH: 750
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is a, c, g, or t

<400> SEQUENCE: 4
atggcccagg tgcagntggt ggagtctggg ggaggcttgg tacagcctgg ggggtccctg    60
agactctcct gtgcagcctc tggattcacc ttcagtagtt atgaaatgaa ctgggtccgc   120
caggctccag gaaggggct ggagtgggtt tcatacatta gtagtagtgg tagtaccata   180
tactacgcag actctgtgaa gggccgattc accatctcca gagacaattc caagaacacg   240
ctgtatctgc aaatgaacag cctgagagct gaggacacgg ctgtgtatta ctgtgcgagt   300
ggggactata tggacgtctg ggggccaggggg accacggtca ccgtctcctc atcggcctcg   360
```

```
ggggccgaat tgggcggcgg cggctccgga ggaggaggat ctggtggtgg tggttcgact    420
agtgacatcc agttgaccca gtctccatcc tccctgtctg catctgttgg agacagagtc    480
accatcactt gccaggcgag tcaggacatt agcaactatt taaattggta tcagcagaaa    540
ccagggaaag cccctaagct cctgatgtac gatgcatcca atttggaaac aggggtccca    600
tcaaggttca gtggaagtgg atctgggaca gattttactt tcaccatcag cagcctgcag    660
cctgaagatt ttgcaacata ttactgtcaa cagtctgata atctcccgta cacttttggc    720
caggggacca agtggatat caaacgctcg                                     750
```

<210> SEQ ID NO 5
<211> LENGTH: 372
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is a, c, g, or t

<400> SEQUENCE: 5

```
atggcccagg tgcagntggt ggagtctggg ggaggcttgg tacagcctgg ggggtccctg    60
agactctcct gtgcagcctc tggattcacc ttcagtagtt atgaaatgaa ctgggtccgc    120
caggctccag gaaggggct ggagtgggtt tcatacatta gtagtagtgg tagtaccata    180
tactacgcag actctgtgaa gggccgattc accatctcca gagacaattc caagaacacg    240
ctgtatctgc aaatgaacag cctgagagct gaggacacgg ctgtgtatta ctgtgcgagt    300
ggggactata tggacgtctg ggccagggg accacggtca ccgtctcctc atcggcctcg    360
ggggccgaat tg                                                        372
```

<210> SEQ ID NO 6
<211> LENGTH: 333
<212> TYPE: DNA
<213> ORGANISM: Homo sapiens

<400> SEQUENCE: 6

```
actagtgaca tccagttgac ccagtctcca tcctccctgt ctgcatctgt tggagacaga    60
gtcaccatca cttgccaggc gagtcaggac attagcaact atttaaattg gtatcagcag    120
aaaccaggga aagcccctaa gctcctgatg tacgatgcat ccaatttgga aacaggggtc    180
ccatcaaggt tcagtggaag tggatctggg acagattttta ctttcaccat cagcagcctg    240
cagcctgaag attttgcaac atattactgt caacagtctg ataatctccc gtacactttt    300
ggccagggga ccaaagtgga tatcaaacgc tcg                                 333
```

<210> SEQ ID NO 7
<211> LENGTH: 45
<212> TYPE: DNA
<213> ORGANISM: Artificial
<220> FEATURE:
<223> OTHER INFORMATION: completely synthesized

<400> SEQUENCE: 7

```
ggcggcggcg gctccggagg aggaggatct ggtggtggtg gttcg                    45
```

<210> SEQ ID NO 8
<211> LENGTH: 257
<212> TYPE: PRT
<213> ORGANISM: Homo sapiens

<400> SEQUENCE: 8

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Glu Met Asn Trp Val Arg Gln Ala Pro Gly Lys Gly Leu Glu
        35                  40                  45

Trp Val Ser Tyr Ile Ser Ser Gly Ser Thr Ile Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Ser Gly Asp Tyr Met Asp Val Trp Gly Gln Gly Thr Thr
                100                 105                 110

Val Thr Val Ser Ser Ala Ser Gly Ala Glu Leu Gly Gly Gly
            115                 120                 125

Ser Gly Gly Gly Gly Ser Gly Gly Gly Ser Thr Ser Asp Ile Gln
    130                 135                 140

Leu Thr Gln Ser Pro Ser Ser Leu Ser Ala Ser Val Gly Asp Arg Val
145                 150                 155                 160

Thr Ile Thr Cys Gln Ala Ser Gln Asp Ile Ser Asn Tyr Leu Asn Trp
                165                 170                 175

Tyr Gln Gln Lys Pro Gly Lys Ala Pro Lys Leu Leu Met Tyr Asp Ala
                180                 185                 190

Ser Asn Leu Glu Thr Gly Val Pro Ser Arg Phe Ser Gly Ser Gly Ser
        195                 200                 205

Gly Thr Asp Phe Thr Phe Thr Ile Ser Ser Leu Gln Pro Glu Asp Phe
    210                 215                 220

Ala Thr Tyr Tyr Cys Gln Gln Ser Asp Asn Leu Pro Tyr Thr Phe Gly
225                 230                 235                 240

Gln Gly Thr Lys Val Asp Ile Lys Arg Ser Ser His His His His
                245                 250                 255

His

<210> SEQ ID NO 9
<211> LENGTH: 124
<212> TYPE: PRT
<213> ORGANISM: Homo sapiens

<400> SEQUENCE: 9

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Glu Met Asn Trp Val Arg Gln Ala Pro Gly Lys Gly Leu Glu
        35                  40                  45

Trp Val Ser Tyr Ile Ser Ser Gly Ser Thr Ile Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Ser Gly Asp Tyr Met Asp Val Trp Gly Gln Gly Thr Thr
                100                 105                 110

Val Thr Val Ser Ser Ala Ser Gly Ala Glu Leu
        115                 120

<210> SEQ ID NO 10
<211> LENGTH: 111
<212> TYPE: PRT
<213> ORGANISM: Homo sapiens

<400> SEQUENCE: 10

Thr Ser Asp Ile Gln Leu Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Met Tyr Asp Ala Ser Asn Leu Glu Thr Gly Val Pro Ser Arg Phe
    50                  55                  60

Ser Gly Ser Gly Ser Gly Thr Asp Phe Thr Phe Thr Ile Ser Ser Leu
65                  70                  75                  80

Gln Pro Glu Asp Phe Ala Thr Tyr Tyr Cys Gln Gln Ser Asp Asn Leu
                85                  90                  95

Pro Tyr Thr Phe Gly Gln Gly Thr Lys Val Asp Ile Lys Arg Ser
            100                 105                 110

<210> SEQ ID NO 11
<211> LENGTH: 250
<212> TYPE: PRT
<213> ORGANISM: Homo sapiens

<400> SEQUENCE: 11

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Glu Met Asn Trp Val Arg Gln Ala Pro Gly Lys Gly Leu Glu
        35                  40                  45

Trp Val Ser Tyr Ile Ser Ser Ser Gly Ser Thr Ile Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Ser Gly Asp Tyr Met Asp Val Trp Gly Gln Gly Thr Thr
            100                 105                 110

Val Thr Val Ser Ser Ala Ser Gly Ala Glu Leu Gly Gly Gly
        115                 120                 125

Ser Gly Gly Gly Ser Gly Gly Gly Ser Thr Ser Asp Ile Gln
    130                 135                 140

Leu Thr Gln Ser Pro Ser Ser Leu Ser Ala Ser Val Gly Asp Arg Val
145                 150                 155                 160

Thr Ile Thr Cys Gln Ala Ser Gln Asp Ile Ser Asn Tyr Leu Asn Trp
                165                 170                 175

Tyr Gln Gln Lys Pro Gly Lys Ala Pro Lys Leu Leu Met Tyr Asp Ala
            180                 185                 190

Ser Asn Leu Glu Thr Gly Val Pro Ser Arg Phe Ser Gly Ser Gly Ser
        195                 200                 205

Gly Thr Asp Phe Thr Phe Thr Ile Ser Ser Leu Gln Pro Glu Asp Phe
    210                 215                 220

Ala Thr Tyr Tyr Cys Gln Gln Ser Asp Asn Leu Pro Tyr Thr Phe Gly
225                 230                 235                 240

Gln Gly Thr Lys Val Asp Ile Lys Arg Ser
            245                 250

<210> SEQ ID NO 12
<211> LENGTH: 15
<212> TYPE: PRT
<213> ORGANISM: Artificial
<220> FEATURE:
<223> OTHER INFORMATION: completely synthesized

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 1289
<212> TYPE: DNA
<213> ORGANISM: Homo sapiens

<400> SEQUENCE: 13
cgtgtacggt gggaggtcta tataagcaga gctttctggc taactagaga acccactgct      60
tactggcacg tggaaattaa tacgacgtgg ccaccatggg atggagctgt atcatcctct     120
tcttggtagc aacagctaca ggtaaggggt taacagtagc aggcttgagg tctggacata     180
tatatgggtg acaatgacat ccactttgcc tttctctcca caggcgcgca ctccactagt     240
gacatccagt tgacccagtc tccatcctcc ctgtctgcat ctgttggaga cagagtcacc     300
atcacttgcc aggcgagtca ggacattagc aactatttaa attggtatca gcagaaacca     360
gggaaagccc ctaagctcct gatgtacgat gcatccaatt tggaaacagg gtcccatca      420 aggttcagtg gaagtggatc tgggacagat tttactttca ccatcagcag cctgcagcct     480
gaagattttg caacatatta ctgtcaacag tctgataatc tcccgtacac ttttggccag     540
gggaccaaag tggatatcaa acgctcgcgt acggtggctg caccatctgt cttcatcttc     600
ccgccatctg atgagcagtt gaaatctgga actgcctctg ttgtgtgcct gctgaataac     660
ttctatccca gagaggccaa agtacagtgg aaggtggata acgccctcca atcgggtaac     720
tcccaggaga gtgtcacaga gcaggacagc aaggacagca cctacagcct cagcagcacc     780
ctgacgctga gcaaagcaga ctacgagaaa cacaaagtct acgcctgcga agtcacccat     840
cagggcctga gctcgcccgt cacaaagagc ttcaacaggg gagagtgtta ataatctaga     900
gggcccgttt tttaaaccgc tgatcagcct cgactgtgcc ttctagttgc agccatctg      960 ttgtttgccc ctcccccgtg ccttccttga ccctggaagg tgccactccc actgtccttt    1020
cctaataaaa tgaggaaatt gcatcgcatt gtctgagtag gtgtcattct attctggggg    1080
gtggggtggg gcaggacagc aaggggggagg attgggaaga caatagcagg catgctgggg    1140
atgcggtggg ctctatggct tctgaggcgg aaagaaccag ctggggctct aggggggtatc    1200 cccacgcgcc ctgtagcggc gcattaagcg cggcgggtgt ggtggttacg cgcagcgtga    1260
ccgctacact tgccagcgcc ctagcgccc                                      1289

<210> SEQ ID NO 14
<211> LENGTH: 781
<212> TYPE: DNA

```
<213> ORGANISM: Homo sapiens
<220> FEATURE:
<221> NAME/KEY: Unsure
<222> LOCATION: (7)..(7)
<223> OTHER INFORMATION: n at position 7 can be any nucleotide,
<220> FEATURE:
<221> NAME/KEY: Unsure
<222> LOCATION: (8)..(8)
<223> OTHER INFORMATION: n at position 8 can be any nucleotide,
<220> FEATURE:
<221> NAME/KEY: Unsure
<222> LOCATION: (18)..(18)
<223> OTHER INFORMATION: n at position 18 can be any nucleotide,
<220> FEATURE:
<221> NAME/KEY: Unsure
<222> LOCATION: (38)..(38)
<223> OTHER INFORMATION: n at position 38 can be any nucleotide,
<220> FEATURE:
<221> NAME/KEY: Unsure
<222> LOCATION: (686)..(686)
<223> OTHER INFORMATION: n at position 686 can be any nucleotide,
<220> FEATURE:
<221> NAME/KEY: Unsure
<222> LOCATION: (687)..(687)
<223> OTHER INFORMATION: n at position 687 can be any nucleotide,
<220> FEATURE:
<221> NAME/KEY: Unsure
<222> LOCATION: (688)..(688)
<223> OTHER INFORMATION: n at position 688 can be any nucleotide,
<220> FEATURE:
<221> NAME/KEY: Unsure
<222> LOCATION: (730)..(730)
<223> OTHER INFORMATION: n at position 730 can be any nucleotide,
<220> FEATURE:
<221> NAME/KEY: Unsure
<222> LOCATION: (736)..(736)
<223> OTHER INFORMATION: n at position 736 can be any nucleotide,
<220> FEATURE:
<221> NAME/KEY: Unsure
<222> LOCATION: (737)..(737)
<223> OTHER INFORMATION: n at position 737 can be any nucleotide,
<220> FEATURE:
<221> NAME/KEY: Unsure
<222> LOCATION: (738)..(738)
<223> OTHER INFORMATION: n at position 738 can be any nucleotide,
<220> FEATURE:
<221> NAME/KEY: Unsure
<222> LOCATION: (755)..(755)
<223> OTHER INFORMATION: n at position 755 can be any nucleotide,
<220> FEATURE:
<221> NAME/KEY: Unsure
<222> LOCATION: (758)..(758)
<223> OTHER INFORMATION: n at position 758 can be any nucleotide,
<220> FEATURE:
<221> NAME/KEY: Unsure
<222> LOCATION: (761)..(761)
<223> OTHER INFORMATION: n at position 761 can be any nucleotide,

<400> SEQUENCE: 14
gagcttnntg gctaactnga gaacccactg cttactgnca cgtggaaatt aatacgacgt        60
ggccaccatg ggatggagct gtatcatcct cttcttggta gcaacagcta caggtaaggg       120
gttaacagta gcaggcttga ggtctggaca tatatatggg tgacaatgac atccactttg       180
cctttctctc cacaggcgcg cactccatgg cccaggtgca gctggtggag tctgggggag       240
gcttggtaca gcctgggggg tccctgagac tctcctgtgc agcctctgga ttcaccttca       300
gtagttatga aatgaactgg gtccgccagg ctccagggaa ggggctggag tgggtttcat       360
acattagtag tagtggtagt accatatact acgcagactc tgtgaagggc cgattcacca       420
tctccagaga caattccaag aacacgctgt atctgcaaat gaacagcctg agagctgagg       480
acacggctgt gtattactgt gcgagtgggg actatatgga cgtctggggc caggggacca       540
cggtcaccgt ctcctcagct agcaccaagg gcccatcggt cttccccctg gcaccctcct       600
```

```
ccaagagcac ctctgggggc acagcggccc tgggctgcct ggtcaaggac tacttccccg    660
aaccggtgac ggtgtcgtgg aactcnngc cctgaccagc ggcgtgcaca ccttcccggc    720
tgtcctacan tcctcnnnct ctactccctc agcancgngg ngaccgtgcc ctccagcagc    780
t                                                                    781
```

<210> SEQ ID NO 15
<211> LENGTH: 179
<212> TYPE: PRT
<213> ORGANISM: Homo sapiens
<220> FEATURE:
<221> NAME/KEY: UNSURE
<222> LOCATION: (177)..(177)
<223> OTHER INFORMATION: Xaa at position 177 can be any amino acid
<220> FEATURE:
<221> NAME/KEY: UNSURE
<222> LOCATION: (178)..(178)
<223> OTHER INFORMATION: Xaa at position 178 can be any amino acid

<400> SEQUENCE: 15

```
Met Gly Asp Asn Asp Ile His Phe Ala Phe Leu Ser Thr Gly Ala His
1               5                   10                  15

Ser Met Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Glu Met Asn Trp Val Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ser Gly Asp Tyr Met Asp Val Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Xaa Xaa Pro
```

<210> SEQ ID NO 16
<211> LENGTH: 530
<212> TYPE: PRT
<213> ORGANISM: Mus musculus

<400> SEQUENCE: 16

```
Met Ala Arg Phe Arg Arg Ala Asp Leu Ala Ala Ala Gly Val Met Leu
1               5                   10                  15

Leu Cys His Phe Leu Thr Asp Arg Phe Gln Phe Ala His Gly Glu Pro
            20                  25                  30

Gly His His Thr Asn Asp Trp Ile Tyr Glu Val Thr Asn Ala Phe Pro
        35                  40                  45

Trp Asn Glu Glu Gly Val Glu Val Asp Ser Gln Ala Tyr Asn His Arg
    50                  55                  60
```

```
Trp Lys Arg Asn Val Asp Pro Phe Lys Ala Val Asp Thr Asn Arg Ala
 65                  70                  75                  80

Ser Met Gly Gln Ala Ser Pro Glu Ser Lys Gly Phe Thr Asp Leu Leu
                 85                  90                  95

Leu Asp Asp Gly Gln Asp Asn Asn Thr Gln Ile Glu Glu Asp Thr Asp
                100                 105                 110

His Asn Tyr Tyr Ile Ser Arg Ile Tyr Gly Pro Ala Asp Ser Ala Ser
            115                 120                 125

Arg Asp Leu Trp Val Asn Ile Asp Gln Met Glu Lys Asp Lys Val Lys
130                 135                 140

Ile His Gly Ile Leu Ser Asn Thr His Arg Gln Ala Ala Arg Val Asn
145                 150                 155                 160

Leu Ser Phe Asp Phe Pro Phe Tyr Gly His Phe Leu Asn Glu Val Thr
                165                 170                 175

Val Ala Thr Gly Gly Phe Ile Tyr Thr Gly Glu Val Val His Arg Met
                180                 185                 190

Leu Thr Ala Thr Gln Tyr Ile Ala Pro Leu Met Ala Asn Phe Asp Pro
            195                 200                 205

Ser Val Ser Arg Asn Ser Thr Val Arg Tyr Phe Asp Asn Gly Thr Ala
210                 215                 220

Leu Val Val Gln Trp Asp His Val His Leu Gln Asp Asn Tyr Asn Leu
225                 230                 235                 240

Gly Ser Phe Thr Phe Gln Ala Thr Leu Leu Met Asp Gly Arg Ile Ile
                245                 250                 255

Phe Gly Tyr Lys Glu Ile Pro Val Leu Val Thr Gln Ile Ser Ser Thr
                260                 265                 270

Asn His Pro Val Lys Val Gly Leu Ser Asp Ala Phe Val Val His
            275                 280                 285

Arg Ile Gln Gln Ile Pro Asn Val Arg Arg Thr Ile Tyr Glu Tyr
290                 295                 300

His Arg Val Glu Leu Gln Met Ser Lys Ile Thr Asn Ile Ser Ala Val
305                 310                 315                 320

Glu Met Thr Pro Leu Pro Thr Cys Leu Gln Phe Asn Gly Cys Gly Pro
                325                 330                 335

Cys Val Ser Ser Gln Ile Gly Phe Asn Cys Ser Trp Cys Ser Lys Leu
                340                 345                 350

Gln Arg Cys Ser Ser Gly Phe Asp Arg His Arg Gln Asp Trp Val Asp
            355                 360                 365

Ser Gly Cys Pro Glu Glu Val Gln Ser Lys Glu Lys Met Cys Glu Lys
            370                 375                 380

Thr Glu Pro Gly Glu Thr Ser Gln Thr Thr Thr Ser His Thr Thr
385                 390                 395                 400

Thr Met Gln Phe Arg Val Leu Thr Thr Arg Arg Ala Val Thr Ser
                405                 410                 415

Gln Met Pro Thr Ser Leu Pro Thr Glu Asp Thr Lys Ile Ala Leu
            420                 425                 430

His Leu Lys Asp Ser Gly Ala Ser Thr Asp Asp Ser Ala Ala Glu Lys
            435                 440                 445

Lys Gly Gly Thr Leu His Ala Gly Leu Ile Val Gly Ile Leu Ile Leu
            450                 455                 460

Val Leu Ile Ile Ala Ala Ala Ile Leu Val Thr Val Tyr Met Tyr His
465                 470                 475                 480
```

-continued

His Pro Thr Ser Ala Ala Ser Ile Phe Phe Ile Glu Arg Arg Pro Ser
                485                 490                 495

Arg Trp Pro Ala Met Lys Phe Arg Gly Ser Gly His Pro Ala Tyr
        500                 505                 510

Ala Glu Val Glu Pro Val Gly Glu Lys Glu Gly Phe Ile Val Ser Glu
        515                 520                 525

Gln Cys
    530

<210> SEQ ID NO 17
<211> LENGTH: 529
<212> TYPE: PRT
<213> ORGANISM: Homo sapiens

<400> SEQUENCE: 17

Met Ala Arg Phe Pro Lys Ala Asp Leu Ala Ala Gly Val Met Leu
1               5                   10                  15

Leu Cys His Phe Phe Thr Asp Gln Phe Gln Phe Ala Asp Gly Lys Pro
                20                  25                  30

Gly Asp Gln Ile Leu Asp Trp Gln Tyr Gly Val Thr Gln Ala Phe Pro
            35                  40                  45

His Thr Glu Glu Glu Val Glu Val Asp Ser His Ala Tyr Ser His Arg
        50                  55                  60

Trp Lys Arg Asn Leu Asp Phe Leu Lys Ala Val Asp Thr Asn Arg Ala
65                  70                  75                  80

Ser Val Gly Gln Asp Ser Pro Glu Pro Arg Ser Phe Thr Asp Leu Leu
                85                  90                  95

Leu Asp Asp Gly Gln Asp Asn Asn Thr Gln Ile Glu Glu Asp Thr Asp
                100                 105                 110

His Asn Tyr Tyr Ile Ser Arg Ile Tyr Gly Pro Ser Asp Ser Ala Ser
            115                 120                 125

Arg Asp Leu Trp Val Asn Ile Asp Gln Met Glu Lys Asp Lys Val Lys
        130                 135                 140

Ile His Gly Ile Leu Ser Asn Thr His Arg Gln Ala Ala Arg Val Asn
145                 150                 155                 160

Leu Ser Phe Asp Phe Pro Phe Tyr Gly His Phe Leu Arg Glu Ile Thr
                165                 170                 175

Val Ala Thr Gly Gly Phe Ile Tyr Thr Gly Glu Val Val His Arg Met
            180                 185                 190

Leu Thr Ala Thr Gln Tyr Ile Ala Pro Leu Met Ala Asn Phe Asp Pro
        195                 200                 205

Ser Val Ser Arg Asn Ser Thr Val Arg Tyr Phe Asp Asn Gly Thr Ala
    210                 215                 220

Leu Val Val Gln Trp Asp His Val His Leu Gln Asp Asn Tyr Asn Leu
225                 230                 235                 240

Gly Ser Phe Thr Phe Gln Ala Thr Leu Leu Met Asp Gly Arg Ile Ile
                245                 250                 255

Phe Gly Tyr Lys Glu Ile Pro Val Leu Val Thr Gln Ile Ser Ser Thr
            260                 265                 270

Asn His Pro Val Lys Val Gly Leu Ser Asp Ala Phe Val Val His
        275                 280                 285

Arg Ile Gln Gln Ile Pro Asn Val Arg Arg Thr Ile Tyr Glu Tyr
    290                 295                 300

His Arg Val Glu Leu Gln Met Ser Lys Ile Thr Asn Ile Ser Ala Val
305                 310                 315                 320

Glu Met Thr Pro Leu Pro Thr Cys Leu Gln Phe Asn Arg Cys Gly Pro
            325                 330                 335

Cys Val Ser Ser Gln Ile Gly Phe Asn Cys Ser Trp Cys Ser Lys Leu
            340                 345                 350

Gln Arg Cys Ser Ser Gly Phe Asp Arg His Arg Gln Asp Trp Val Asp
            355                 360                 365

Ser Gly Cys Pro Glu Glu Ser Lys Glu Lys Met Cys Glu Asn Thr Glu
            370                 375                 380

Pro Val Glu Thr Ser Ser Arg Thr Thr Thr Thr Val Gly Ala Thr Thr
385                 390                 395                 400

Thr Gln Phe Arg Val Leu Thr Thr Thr Arg Arg Ala Val Thr Ser Gln
            405                 410                 415

Phe Pro Thr Ser Leu Pro Thr Glu Asp Asp Thr Lys Ile Ala Leu His
            420                 425                 430

Leu Lys Asp Asn Gly Ala Ser Thr Asp Ser Ala Ala Glu Lys Lys
            435                 440                 445

Gly Gly Thr Leu His Ala Gly Leu Ile Ile Gly Ile Leu Ile Leu Val
            450                 455                 460

Leu Ile Val Ala Thr Ala Ile Leu Val Thr Val Tyr Met Tyr His His
465                 470                 475                 480

Pro Thr Ser Ala Ala Ser Ile Phe Phe Ile Glu Arg Arg Pro Ser Arg
            485                 490                 495

Trp Pro Ala Met Lys Phe Arg Arg Gly Ser Gly His Pro Ala Tyr Ala
            500                 505                 510

Glu Val Glu Pro Val Gly Glu Lys Glu Gly Phe Ile Val Ser Glu Gln
            515                 520                 525

Cys

<210> SEQ ID NO 18
<211> LENGTH: 80
<212> TYPE: PRT
<213> ORGANISM: Homo sapiens

<400> SEQUENCE: 18

Asp Gly Lys Pro Gly Asp Gln Ile Leu Asp Trp Gln Tyr Gly Val Thr
1               5                   10                  15

Gln Ala Phe Pro His Thr Glu Glu Val Glu Val Asp Ser His Ala
            20                  25                  30

Tyr Ser His Arg Trp Lys Arg Asn Leu Asp Phe Leu Lys Ala Val Asp
            35                  40                  45

Thr Asn Arg Ala Ser Val Gly Gln Asp Ser Pro Glu Pro Arg Ser Phe
        50                  55                  60

Thr Asp Leu Leu Leu Asp Gly Gln Asp Asn Asn Thr Gln Ile Glu
65                  70                  75                  80

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                   70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
             195                 200                 205

Lys Ala Leu Pro Ala Pro Ile Glu Lys Thr Ile Ser Lys Ala Lys Gly
         210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
                 260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
         290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                 325                 330
```

ANTIBODIES TO TUMOR ENDOTHELIAL MARKER 7R

CROSS REFERENCE TO RELATED APPLICATIONS

This application is a continuation of U.S. patent application Ser. No. 13/697,024 filed Nov. 9, 2012, which is the U.S. National Phase of PCT Application No. PCT/US2011/036124 filed on May 11, 2011, and claims priority to U.S. Provisional Application No. 61/333,554 filed on May 11, 2010, the entire contents of each application are incorporated by reference herein, in their entirety and for all purposes.

STATEMENT OF GOVERNMENT SUPPORT

The inventions described herein were made, in part, with funds obtained from the National Cancer Institute, Grant No. NCI R01 CA50633. The U.S. government may have certain rights in these inventions.

REFERENCE TO A SEQUENCE LISTING

This application includes a Sequence Listing submitted electronically as a text file named TEM7R PCT-Sequence Listing.txt, created on May 10, 2011, with a size of 31,000 bytes. The Sequence Listing is incorporated by reference herein.

FIELD OF THE INVENTION

The invention relates generally to the field of immunology. More particularly, the invention relates to antibodies to the tumor endothelial marker 7R, and methods for using such antibodies as immunotherapeutics against tumor cells and tumor vascular cells expressing this marker.

BACKGROUND OF THE INVENTION

Various publications, including patents, published applications, technical articles and scholarly articles are cited throughout the specification. Each of these cited publications is incorporated by reference herein, in its entirety and for all purposes.

Tumor associated blood vessels offer numerous tumor specific targets for therapy. The existence of novel genes expressed in human and murine tumor endothelium has been reported (St Croix, B et al. (2000) Science 289:1197-202; and, Carson-Walter, E B et al. (2001) Cancer Res. 61:6649-55). Gene expression patterns of endothelial cells derived from blood vessels in normal and malignant colorectal tumors were compared by serial analysis of gene expression (SAGE), and 46 genes were identified as specifically up-regulated in tumor-associated endothelium.

Further analysis of these tumor endothelial markers (TEM) showed that the genes for four of these proteins encode putative extracellular domains and contain transmembrane motifs. Each TEM has human and murine counterparts with considerable sequence homology. Previously, in situ hybridization analysis of human colorectal cancer showed that TEM7R and TEM8 are clearly expressed in the endothelial cells of the tumor stroma but not in the endothelial cells of normal colonic tissue (Carson-Walter, 2001 Cancer Res. 61:6649). These genes are attractive as molecularly validated tumor-related endothelial markers.

SUMMARY OF THE INVENTION

The invention provides isolated antibodies that specifically bind to an epitope on the extracellular domain of TEM7R from any species, with human or mouse TEM7R being preferred. The antibodies may include a heavy chain comprising the amino acid sequence encoded by the polynucleotide sequence of SEQ ID NO:5, and/or may include a light chain comprising the amino acid sequence encoded by the polynucleotide sequence of SEQ ID NO:6. The antibody may comprise any form or structure, and in some aspects is a monoclonal antibody, while in other aspects is a single chain Fv. A single chain Fv may comprise the amino acid sequence of SEQ ID NO:11 or the amino acid sequence encoded by the polynucleotide sequence of SEQ ID NO:4. The antibody may be a domain antibody comprising a heavy chain domain. The antibody may be a domain antibody comprising a light chain domain. The antibody may be chimeric, humanized, or fully human. The antibody may be conjugated to a chemotherapeutic agent, toxin, and/or a detectable label. The antibody may be in a composition with an acceptable carrier.

The antibody preferably has strong affinity for the epitope. The affinity ($K_d$) may be less than about $1 \times 10^{-5}$ M, less than about $1 \times 10^{-6}$ M, less than about $1 \times 10^{-7}$ M, less than about $1 \times 10^{-8}$ M, less than about $1 \times 10^{-9}$ M, or less than about $1 \times 10^{-10}$ M. Cells capable of expressing the antibodies, including hybridomas, transformed cells, and stable cell lines, are also provided.

The invention also features polynucleotides encoding antibodies that specifically bind to an epitope on the extracellular domain of TEM7R. The heavy chain of the antibodies may be encoded by the nucleic acid sequence of SEQ ID NO: 5, or the heavy chain may comprise the amino acid sequence of SEQ ID NO:9. The light chain of the antibodies may be encoded by the nucleic acid sequence of SEQ ID NO: 6, or the light chain may comprise the amino acid sequence of SEQ ID NO:10. The antibodies may be a single chain Fv and the single chain Fv may be encoded by the polynucleotide sequence of SEQ ID NO:3 or SEQ ID NO:4. The polynucleotides may encode the heavy chain of an antibody that specifically binds to an epitope on the extracellular domain of TEM7R, wherein the heavy chain comprises an amino acid sequence encoded by the polynucleotide sequence of SEQ ID NO:5, or comprises the amino acid sequence of SEQ ID NO:9. The polynucleotides may encode the light chain of an antibody that specifically binds to an epitope on the extracellular domain of TEM7R, wherein the light chain comprises an amino acid sequence encoded by the polynucleotide sequence of SEQ ID NO:6, or comprises the amino acid sequence of SEQ ID NO:10. Polynucleotide variants are also featured. Vectors comprising the polynucleotides and cells transformed or otherwise containing the vectors are also provided.

Polypeptide variants are also featured. The heavy chain of the antibody may comprise an amino acid sequence having at least about 95% sequence identity with the amino acid sequence of SEQ ID NO:9. The light chain of the antibody may comprise an amino acid sequence having at least about 95% sequence identity with the amino acid sequence of SEQ ID NO:10.

The invention also features methods for inhibiting angiogenesis by a tumor. In general, the methods comprise administering to the tumor or otherwise contacting the tumor with a composition comprising an antibody that specifically binds to an epitope on the extracellular domain of TEM7R and a pharmaceutically acceptable carrier, in an amount effective to inhibit angiogenesis. The composition may be administered to the vascular endothelium of the tumor. The antibody may be internalized by a vascular endothelial cell or a tumor cell. The antibody may be conjugated to a chemotherapeutic agent, toxin, or radioisotope. The composition may further comprise a chemotherapeutic agent, toxin, or radiolabel.

The invention also features kits for carrying out any of the methods described and/or exemplified herein. A kit may comprise an antibody that specifically binds to an epitope on the extracellular domain of TEM7R and instructions for using the kit in the method, for example, a method for inhibiting angiogenesis of a tumor. The kit may further comprise at least one chemotherapeutic agent or at least one detectable label.

BRIEF DESCRIPTION OF THE DRAWINGS

FIGS. 1b-1e show raw SPR data.

DETAILED DESCRIPTION OF THE INVENTION

Figure 1A:
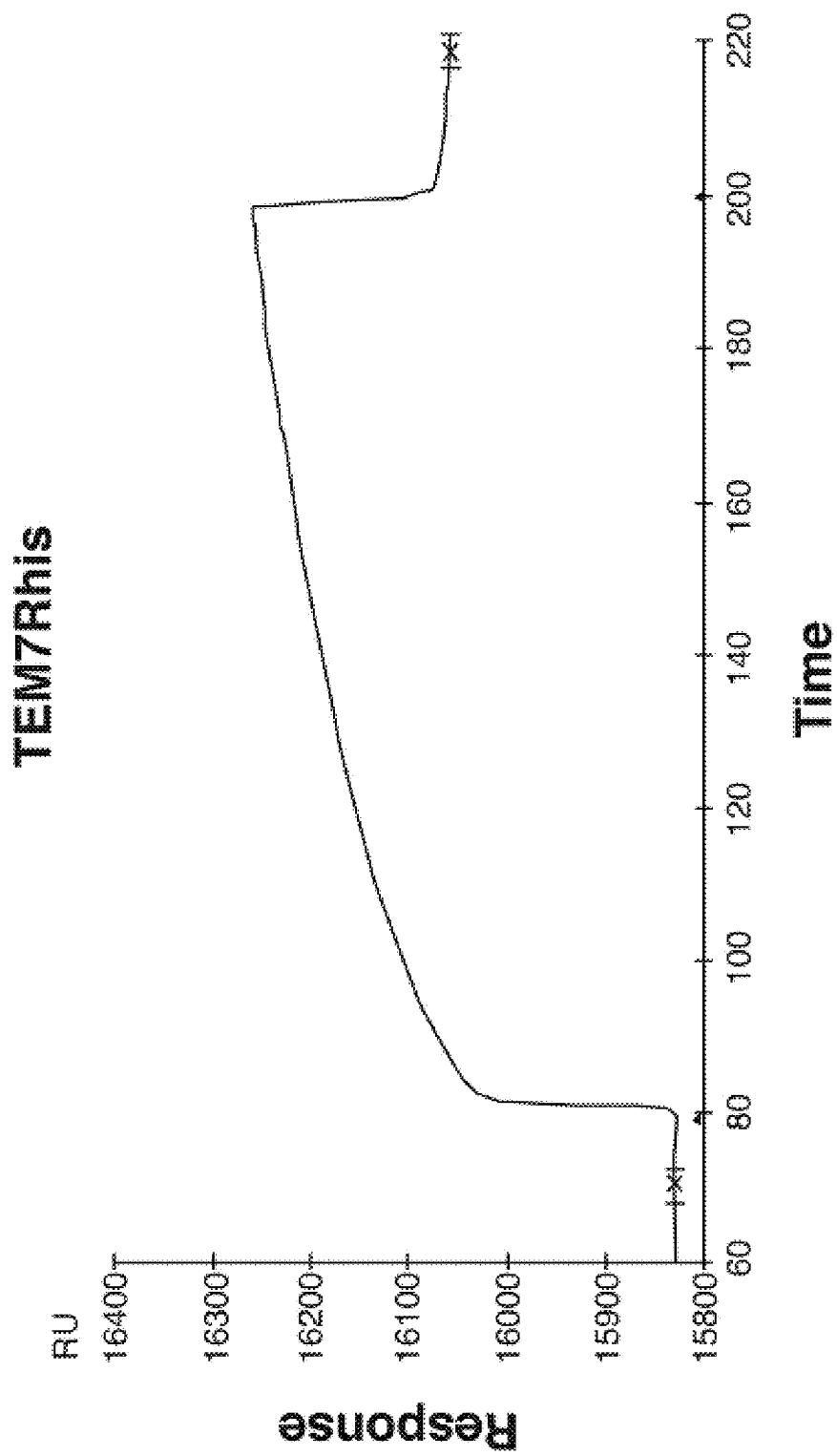
FIG. 1a shows Biacore™ surface plasmon resonance (SPR) for clone 4 (scFv#4).

Various terms relating to aspects of the present invention are used throughout the specification and claims. Such terms are to be given their ordinary meaning in the art, unless otherwise indicated. Other specifically defined terms are to be construed in a manner consistent with the definition provided herein.

The terms "subject" or "patient" are used interchangeably and refer to any animal. Mammals are preferred, and include companion and farm mammals, as well as rodents, including mice, rabbits, and rats, and other rodents. Primates are more preferred, and human beings are highly preferred.

A molecule such as an antibody has been "isolated" if it has been altered and/or removed from its natural environment by the hand of a human being.

As used herein, the singular forms "a," "an," and "the" include plural referents unless expressly stated otherwise.

The term "about" as used herein is meant to encompass variations of 20%, 10%, 5%, 2%, 1%, 0.5%, or 0.1% higher or lower than the specified value.

"TEM7R" refers to tumor endothelial marker 7-related precursor, from any species. TEM7R is also known as plexin domain-containing protein 2 (PLXDC2). Human and mouse TEM7R are highly preferred.

"Angiogenesis" refers to the formation of new blood vessels.

"Neovascularization" refers to a pathological proliferation of new blood vessels in a tissue or organ that normally does not contain blood vessels, or a pathological proliferation of blood vessels of a different type or quantity than normal for a particular tissue or organ.

"Epitope" refers to an immunological determinant of an antigen that serves as an antibody-binding site. The epitope may be linear or conformational.

It has been observed in accordance with the present invention that antibodies that specifically bind to an epitope on the extracellular domain of TEM7R target TEM7R on tumor cells, and are capable of localizing to tumor cells in vivo. It has been further observed that such antibodies can be internalized by tumor cells and exhibit cytotoxic effects on the tumor, as well as a decrease in blood vessel density. It is believed that such antibodies may be tagged with chemotherapeutic agents and targeted to tumor cells to facilitate tumor death. Accordingly, in one aspect, the invention features antibodies to TEM7R.

The antibodies may comprise any of the five classes of immunoglobulins based on antibody heavy chain structure. For example, the alpha, delta, epsilon, gamma, and mu chains correspond to IgA, IgD, IgE, IgG and IgM isotypes, respectively. The antibodies include all isotypes and synthetic multimers of the four-chain immunoglobulin structure. The antibodies may also comprise the IgY isotype generally found in hen or turkey serum and hen or turkey egg yolk.

The antibodies may be polyclonal, but in some aspects, are not polyclonal. The antibodies preferably are monoclonal.

The antibodies may comprise post-translational modifications or moieties, which may impact antibody activity or stability. These modifications or moieties include, but are not limited to, methylated, acetylated, glycosylated, sulfated, phosphorylated, carboxylated, and amidated moieties and other moieties that are well known in the art. Moieties include any chemical group or combinations of groups commonly found on immunoglobulin molecules in nature, or otherwise added to antibodies by recombinant expression systems, including prokaryotic and eukaryotic expression systems.

The antibodies may comprise derivatives or fragments or portions of antibodies that retain the antigen-binding specificity, and also preferably retain most or all of the affinity, of the parent antibody molecule. For example, derivatives may comprise at least one variable region (either a heavy chain or light chain variable region). Other examples of suitable antibody derivatives and fragments include, without limitation, antibodies with polyepitopic specificity, bispecific antibodies, diabodies, single-chain molecules, as well as Fab, F(ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, dimers consisting of one heavy and one light chain, and other multimers. Single chain Fv antibodies may be multivalent. All antibody isotypes may be used to produce antibody derivatives, fragments, and portions. Antibody derivatives, fragments, and/or portions may be recombinantly produced and expressed by any cell type, prokaryotic or eukaryotic.

The antibody may be a domain antibody (dAb). Domain antibodies include those comprising a single variable antibody domain, including a VH or VL domain which are able to specifically bind to an antigen. A heavy chain domain antibody may comprise a heavy chain having the amino acid sequence of SEQ ID NO:9. A light chain domain antibody may comprise a light chain having the amino acid sequence of SEQ ID NO:10. Domain antibodies may be fused to other polypeptides, including antibody Fc domains such as human IgG1 Fc domains (e.g., SEQ ID NO:19), in order to enhance their half life in vivo or to enhance their therapeutic value.

The antibodies may be derived from any species. For example, the antibodies may be mouse, rat, goat, horse, swine, bovine, camel, chicken, rabbit, donkey, llama, dromedary, shark, or human antibodies, as well as antibodies from any other animal species. For use in the treatment of humans, non-human derived antibodies may be structurally altered to be less antigenic upon administration to a human patient, including by chimerization or humanization.

Thus, in some aspects, the antibodies are chimeric antibodies. Chimeric antibodies include portions from different species. For example, a chimeric antibody may comprise a mouse antigen binding domain coupled to a human Fc domain or other such structural domain. Preferred chimeric antibodies include heavy and light chain variable regions not of human origin and constant regions of human origin. Chimeric antibodies and methods to produce them are well known and established in the art.

In some aspects, the antibodies are humanized antibodies. Humanized antibodies are those wherein the amino acids directly involved in antigen binding, e.g., the complementarity determining regions (CDR), and in some cases the framework regions (FWR), or portions thereof, of the heavy and/or light chains are not of human origin, while the rest of the amino acids in the antibody are human or otherwise of human origin, e.g., a human antibody scaffold. The antibodies may be humanized chimeric antibodies. Direct involvement in antigen binding includes direct participation in the interactions of antibody amino acids with the epitope, as well as indirect participation such as the effects on structural aspects of the antibody combining site that allow other amino acids to be oriented in a position where they are able to directly participate in the interactions with the epitope.

In some aspects, the antibodies are fully human. Fully human antibodies are those where the whole molecule is human or otherwise of human origin, or includes an amino acid sequence identical to a human form of the antibody. Fully human antibodies may be expressed in other organisms (e.g., mice and xenomouse technology) or cells from other organisms transformed with genes encoding human antibodies.

The antibodies may be labeled or conjugated to any chemical or biomolecule moieties. Labeled antibodies may find use in therapeutic, diagnostic, or basic research applications. Such labels/conjugates can be detectable, such as fluorochromes, radiolabels, enzymes, fluorescent proteins, and biotin. The labels/conjugates may be chemotherapeutic agents, toxins, isotopes, and other agents used for treating conditions such as the killing of cancer cells. Chemotherapeutic agents may be any suitable for the purpose to which the antibody is being used. In the case of treating tumors, the agent may be among the class of alkylating agents, antimetabolites, anthracyclines, antibiotics, platinums, plant alkaloids, vinca alkaloids, topoisomerase inhibitors, taxanes, hormones, corticosteroids, epipodophyllotoxins, and other agents known or used to treat any aspect of tumor growth, sustenance, or proliferation, including the killing of the tumor cells or inhibition of angiogenesis or neovascularization of a tumor.

The antibodies may be derivatized by known protecting/blocking groups to prevent proteolytic cleavage or enhance activity or stability.

The antibodies may comprise a heavy chain comprising the amino acid sequence encoded by the nucleic acid sequence of SEQ ID NO:5, or the amino acid sequence of SEQ ID NO:9. The heavy chain amino acid sequence may comprise at least about 95% identity with the amino acid sequence of SEQ ID NO:9 The antibodies may comprise a light chain comprising the amino acid sequence encoded by the nucleic acid sequence of SEQ ID NO:6, or the amino acid sequence of SEQ ID NO:10. The light chain amino acid sequence may comprise at least about 95% identity with the amino acid sequence of SEQ ID NO:10. In some preferred aspects, the antibodies may comprise a heavy chain comprising the amino acid sequence of SEQ ID NO:9 and a light chain comprising the amino acid sequence of SEQ ID NO:10. In some preferred aspects, the antibodies may comprise a heavy chain having an amino acid sequence having at least about 95% identity with the amino acid sequence of SEQ ID NO:9 and a light chain having an amino acid sequence having at least about 95% identity with the amino acid sequence of SEQ ID NO:10.

The antibodies may comprise a single chain Fv molecule (scFv). The scFv may comprise the amino acid sequence of SEQ ID NO:11. The scFv may comprise the amino acid sequence encoded by the nucleic acid sequence of SEQ ID NO:3, or the amino acid sequence encoded by the nucleic acid sequence of SEQ ID NO:4. The scFv may comprise a linker having the amino acid sequence of SEQ ID NO:12, which may be fused between the heavy and light chain amino acid sequences.

Natural sequence variations may exist among heavy and light chains and the genes encoding them, and therefore the person having ordinary skill in the art would expect to find some level of variation within the amino acid sequences, or the genes encoding them, of the antibodies described and exemplified herein. These variants preferably maintain the unique binding properties (e.g., specificity and affinity) of the parent antibody. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The antibodies thus include variants having single or multiple amino acid substitutions, deletions, additions, or replacements that retain the biological properties (e.g., binding specificity and binding affinity) of the parent antibodies. The variants are preferably conservative, but may be non-conservative.

The antibodies include variants having a heavy chain with at least about 90%, at least about 92%, at least about 95%, at least about 96%, at least about 97%, at least about 98%, or at least about 99% identity with the amino acid sequence of SEQ ID NO:9. The antibody variants will specifically bind to an epitope on the extracellular domain of TEM7R with an affinity about equal to the affinity of an antibody having a heavy chain with the amino acid sequence of SEQ ID NO:9.

The antibodies include variants having a light chain with at least about 90%, at least about 92%, at least about 95%, at least about 96%, at least about 97%, at least about 98%, or at least about 99% identity with the amino acid sequence of SEQ ID NO:10. The antibody variants will specifically bind to an epitope on the extracellular domain of TEM7R with an affinity about equal to the affinity of an antibody having a light chain with the amino acid sequence of SEQ ID NO:10. For avoidance of doubt, variations may exist in both the heavy and light chains in a single antibody molecule. Thus, the antibodies may comprise a variant of the heavy chain having the amino acid sequence SEQ ID NO:9 and a variant of the light chain having the amino acid sequence SEQ ID NO:10.

The antibodies preferably have binding affinities for an epitope on the extracellular domain of TEM7R that include a dissociation constant ($K_d$) of less than about $1\times10^{-2}$ M. In some embodiments, the $K_d$ is less than about $1\times10^{-3}$ M. In other embodiments, the $K_d$ is less than about $1\times10^{-4}$ M. In some embodiments, the $K_d$ is less than about $1\times10^{-5}$ M. In still other embodiments, the $K_d$ is less than about $1\times10^{-6}$ M. In other embodiments, the $K_d$ is less than about $1\times10^{-7}$ M. In other embodiments, the $K_d$ is less than about $1\times10^{-8}$ M. In other embodiments, the $K_d$ is less than about $1\times10^{-9}$ M. In other embodiments, the $K_d$ is less than about $1\times10^{-10}$ M. In still other embodiments, the $K_d$ is less than about $1\times10^{-11}$ M. In some embodiments, the $K_d$ is less than about $1\times10^{-12}$ M. In other embodiments, the $K_d$ is less than about $1\times10^{-13}$ M. In other embodiments, the $K_d$ is less than about $1\times10^{-14}$ M. In still other embodiments, the $K_d$ is less than about $1\times10^{-15}$ M. Affinity values refer to those obtained by standard methodologies, including surface plasmon resonance such as Biacore™ analyses.

In some aspects, the antibody competitively inhibits the binding of an antibody having a heavy chain having an amino acid sequence of SEQ ID NO:9. In some aspects, the antibody competitively inhibits the binding of an antibody having a light chain having an amino acid sequence of SEQ ID NO:10. In some aspects, the antibody competitively inhibits the binding of an antibody having a heavy chain having an amino acid sequence of SEQ ID NO:9 and having a light chain having an amino acid sequence of SEQ ID NO:10. In some aspects, the antibody competitively inhibits the binding of the scFv having the amino acid sequence of SEQ ID NO:11.

In some aspects, the antibody may include the proviso that the antibody is not clone 4G10, available as product number H00084898-M01 from Novus Biologicals, and/or with the proviso that the antibody does not bind to the epitope DGKPGDQILDWQYGVTQAFPHTEEEV EVDSHAYSHRWKRNLDFLKAVDTNRASVGQDSPEPRSFTDLLLDDGQDNNTQIE (SEQ ID NO: 18), or with the proviso that the antibody competitively inhibits clone 4G10 binding to SEQ ID NO:18, or with the proviso that the antibody competitively inhibits an antibody binding to SEQ ID NO:18.

Polynucleotide sequences that encode antibodies are featured in the invention. Polynucleotides include, but are not limited to, RNA, DNA, hybrids of RNA and DNA, and single, double, or triple stranded strands of RNA, DNA, or hybrids thereof.

In some aspects, the polynucleotides encode the heavy chain of an antibody that specifically binds to an epitope on the extracellular domain of TEM7R. The heavy chain may comprise an amino acid sequence encoded by the polynucleotide sequence of SEQ ID NO:5. The polynucleotide may comprise SEQ ID NO:5. In some aspects, the polynucleotides encode the light chain of an antibody that specifically binds to an epitope on the extracellular domain of TEM7R. The chain may comprise an amino acid sequence encoded by the polynucleotide sequence of SEQ ID NO:6. The polynucleotide may comprise SEQ ID NO:6. In some aspects, the polynucleotides encode a single chain Fv antibody. The polynucleotides may encode a single chain Fv comprising the amino acid sequence of SEQ ID NO:11. The polynucleotides may comprise the nucleic acid sequence of SEQ ID NO:3 or the nucleic acid sequence of SEQ ID NO:4.

Variants of the polynucleotide sequences are also contemplated by the invention. The variants include at least about 90%, at least about 92%, at least about 95%, at least about 96%, at least about 97%, at least about 98%, or at least about 99% identity with the polynucleotide sequence of SEQ ID NO:3, SEQ ID NO:4, SEQ ID NO:5, SEQ ID NO:6, SEQ ID NO:7, SEQ ID NO:13, or SEQ ID NO:14. Preferably, the antibodies encoded by the polynucleotide variants will specifically bind to an epitope on the extracellular domain of TEM7R with an affinity about equal to the affinity of the parent polynucleotide sequence. Complements of the polynucleotide sequences and the variant polynucleotide sequences are also within the scope of the invention.

Also encompassed within the invention are vectors comprising the polynucleotides of the invention. The vectors may be expression vectors. Recombinant expression vectors containing a sequence encoding a polypeptide of interest are thus provided. The expression vector may contain one or more additional sequences, such as but not limited to regulatory sequences, a selection marker, a purification tag, or a polyadenylation signal. Such regulatory elements may include a transcriptional promoter, enhancers, mRNA ribosomal binding sites, or sequences that control the termination of transcription and translation.

Expression vectors, especially mammalian expression vectors, may include one or more nontranscribed elements, such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a specific host may also be incorporated.

The vectors may be used to transform any of a wide array of host cells well known to those of skill in the art, and preferably host cells capable of expressing antibodies. Vectors include without limitation, plasmids, phagemids, cosmids, baculoviruses, bacmids, bacterial artificial chromosomes (BACs), yeast artificial chromosomes (YACs), and baculovirus, as well as other bacterial, eukaryotic, yeast, and viral vectors. Suitable host cells include without limitation CHO cells, HEK293 cells, or any eukaryotic stable cell line known or produced, and also include bacteria, yeast, and insect cells.

The antibodies may also be produced by hybridoma cells; methods to produce hybridomas being well known and established in the art.

The invention also features compositions. The compositions may comprise any of the antibodies described and/or exemplified herein and an acceptable carrier such as a pharmaceutically acceptable carrier. Suitable carriers include any media that does not interfere with the biological activity of the antibody and preferably is not toxic to a host to which it is administered. The carrier may be an aqueous solution, such as water, saline, or alcohol, or a physiologically compatible buffer, such as Hanks's solution, Ringer's solution, or physiological saline buffer. The carrier may contain formulatory agents, such as suspending, stabilizing and/or dispersing agents.

The compositions may also be formulated in sustained release vehicles or depot preparations. For example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The invention also features methods for inhibiting angiogenesis in a tumor. The methods may be carried out in vitro, in vivo, or in situ.

In some aspects, the methods comprise administering to a tumor an antibody that specifically binds to an epitope on the extracellular domain of TEM7R, or a composition comprising an antibody that specifically binds to an epitope on the extracellular domain of TEM7R and an acceptable carrier, in an amount effective to inhibit angiogenesis. Antibodies include any of those described and exemplified herein.

In some aspects, the methods comprise contacting a tumor cell, tumor cell culture, tumor vasculature cell, tumor vasculature cell culture, tumor tissue, and other tissues and cells with an antibody that specifically binds to an epitope on the extracellular domain of TEM7R, or a composition that comprises an antibody that specifically binds to an epitope on the extracellular domain of TEM7R and an acceptable carrier, in an amount effective to inhibit angiogenesis, wherein the antibody specifically binding to TEM7R inhibits angiogenesis and/or destroys existing tumor blood vessels and/or leads to direct and indirect tumor cell death. Antibodies include those described and exemplified herein.

The antibody or composition may be administered directly to the tumor, including any substructure or location in the tumor. The antibody or composition may be administered proximally to the tumor, including any location not directly in, but proximal to the tumor such that the antibody diffuses to and/or into the tumor, or can be actively targeted to the tumor. The antibody or composition may be administered distally to the tumor, such that the antibody diffuses to and/or into the tumor. Diffusion may be passive (e.g., via blood flow). Proximally or distally administered antibodies or compositions may also be actively targeted to the tumor. In some highly preferred aspects, the composition is administered to the vascular endothelium of the tumor. The antibody may be internalized by a tumor cell or may be internalized by a vascular endothelial cell.

The antibody may be conjugated to a chemotherapeutic agent, toxin, or radioisotope. The composition may include a conjugated or unconjugated antibody and a chemotherapeutic agent, and where a conjugated antibody is used, the conjugated chemotherapeutic agent may be the same as or different from the chemotherapeutic agent separately in the composition. Multiple chemotherapeutic agents may be conjugated and/or included in the composition.

The invention also features methods for imaging and/or detecting tumors. In some aspects, the methods comprise contacting a tumor cell, tumor cell culture, tumor vasculature cell, tumor vasculature cell culture, tumor tissue, and other tissues and cells with an antibody that specifically binds to an epitope on the extracellular domain of TEM7R, and imaging or detecting the tumor cell, tumor cell culture, tumor vasculature cell, tumor vasculature cell culture, tumor tissue. Antibodies include those described and exemplified herein, and the antibodies may be contacted by way of a composition comprising the antibody. The antibody may be conjugated to a detectable label, such as a fluorochrome, radiolabel, enzyme, fluorescent protein, biotin, and other labels, and thus directly used to image or detect the tumor. Alternatively, the antibody may be contacted with a secondary antibody conjugated to such a detectable label. The imaging or detecting may be carried out according to any means suitable in the art and appropriate for the detectable label being used.

The invention also features kits comprising antibodies described and exemplified herein. The kits may be used to supply antibodies and other agents for use in diagnostic, basic research, or therapeutic methods, among others.

In some aspects, a kit comprises an antibody that specifically binds to an epitope on the extracellular domain of TEM7R and instructions for using the kit in a method for inhibiting angiogenesis of a tumor. The kit may further comprise at least one chemotherapeutic agent, which may be conjugated to the antibody or may be separate from the antibody. For unconjugated chemotherapeutic agents, the kit may further comprise agents and instructions for conjugating the chemotherapeutic agent to the antibody. The chemotherapeutic agent need not, however, be conjugated to the antibody and may be intended to be administered to a subject or contacted with a tumor apart from the antibody. The kits may comprise a pharmaceutically acceptable carrier. In the kits, the antibody may be any antibody described or exemplified herein.

The following examples are provided to describe the invention in greater detail. They are intended to illustrate, not to limit, the invention.

Example 1

General Experimental Procedures

A. Cloning and Expression of TEM7R Extracellular Domain.

Figure 1F:
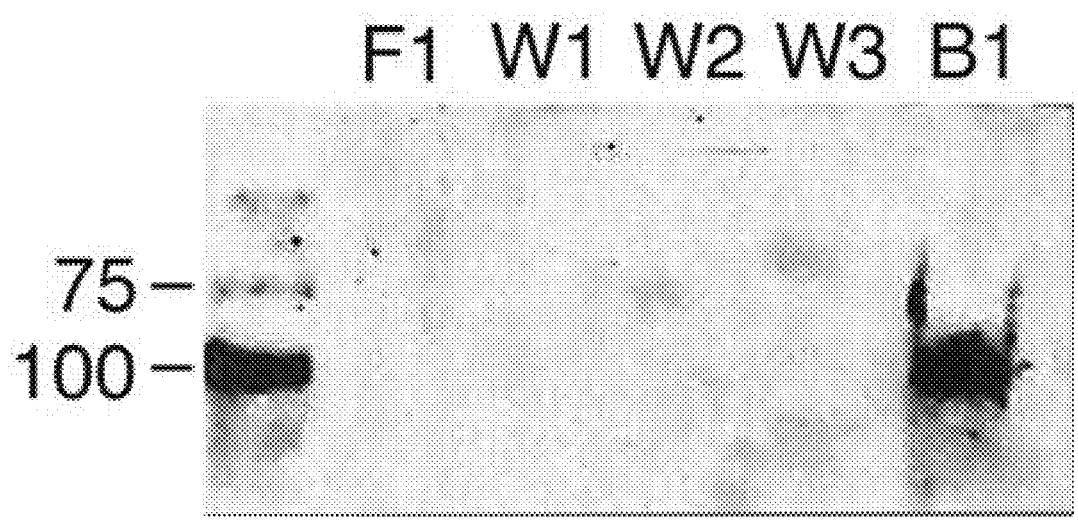
FIG. 1f shows a Western blot showing purified TEM7R. The Western blot was detected using a labeled anti-His antibody.

The putative extracellular domain of the mouse tumor endothelial marker 7R (TEM7R) was cloned from a mouse embryonic RNA library into the pSecTag2/Hygro A expression vector (Invitrogen). Transient transfection of COS7 cells was used to generate TEM7R protein for use in initial experiments. The cDNA encoding the extracellular domain (ECD) of mTEM7R was amplified by RT-PCR, cloned into the pSecTag2/Hygro A vector and stably transfected into HEK293 cells. Because this vector contains the Ig κ signal sequence 5' to the multiple cloning site, the protein product is secreted into the culture media by the host bacteria. The resulting 6×His-tagged protein was purified from culture supernatants by HPLC (1.5 mg/L supernatant) over a HiTrap™ chelating $Ni^{2+}$ column (GE Healthcare Life Sciences) and expression was verified by SDS-PAGE and Western blotting (FIG. 1f).

B. Subtraction Library Panning.

Anti-TEM7R scFv-phage were isolated from a human non-immune scFv phage display library (G. Adams Laboratory) with an approximate size of $1.6×10^{10}$ independent transformants. Prior to panning, TEM7R ECD was coated onto the sides of a Maxisorp™-immunotube (Nunc, Denmark) at a concentration of 20 µg/ml in coating buffer (BupH™ carbonate-bicarbonate buffer, Pierce) at 4° C., overnight. The coated immunotube was then washed 3 times in PBS and blocked with 4% MPBS (skimmed milk dissolved in PBS) at 37° C. for 2 h. 100 µl of the original phage library stock ($1.3×10^{13}$ pfu/ml) was added to 4 ml of 2% MPBS containing 100 µg/ml purified human IgG1 Fc domain in order to compete out binders for the Fc portion of the TEM7R ECD protein.

The mixture was incubated at room temperature for 30 min. before loading into the blocked Immunotube. The coated Immunotube containing the phage was placed on a clinical rotator for 2-3 h at room temperature. The solution containing unbound phage was then decanted out of the Immunotube and the tube was washed 10 times with PBST (PBS, 0.1% Tween-20® (ICI Americas, Inc.)) and 10 times with PBS. The bound phage were then eluted from the immobilized TEM7R ECD by addition of 1 ml of fresh 100 mM triethylamine (TEA, Sigma) and immediately neutralized with 0.5 ml (½ volume) of 1M Tris, pH 7.4. 10 ml of log-phase (0.3-0.5 $O.D_{600}$) TG1 $E.\ coli$ (Stratagene) was then infected with 750 µl of the eluate. The infected $E.\ coli$ were then concentrated to a volume of 1 ml. A 1 µl aliquot was removed and serially diluted in order to determine the titer. The remaining infected $E.\ coli$ were plated on a 25 mm 2×YT-AG plates (2×YT containing 1% glucose, 100 µg/ml ampicillin) overnight at 37° C.

The next day, 6 ml of 2×YT-AG was added to the plates and the $E.\ coli$ lawn was removed by scraping. 100 µl of the bacterial slurry was used as a source for the subsequent round of phage panning and amplification. A total of three rounds of selection were performed, where each was performed as described above except that the stringency of the selection procedure was increased in the $2^{nd}$ and $3^{rd}$ rounds by reducing the quantity of TEM7R ECD coated onto the Immunotube to 10 µg/ml and increasing the number of wash cycles to 20 times with PBST followed by 20 times with PBS.

C. Monophage ELISA.

After the third round of selection, individual colonies were isolated for screening in a monophage ELISA (Kingsbury, G A et al. (1995) Nucleic Acids Res. 23:2563-4) to determine the presence of phage containing anti-TEM7R ECD scFv. Briefly, individual colonies were picked from the 2×YT-AG plates and inoculated into individual wells of a 'master' 96-well plate (Nunclon™ Surface, NUNC, Denmark) containing 180 µl 2×YT-AG medium in each well. The plates were grown overnight in a shaking incubator at 37° C., 180 rpm.

Ten percent of the volume of each well was transferred into corresponding wells of a 'working' 96-well plate (Nunclon™ Surface, NUNC, Denmark) containing 180 µl 2×YT-AG medium in each well. The plate was incubated for 1 hr in a shaking incubator at 37° C., 180 rpm. KO7 helper phage ($10^{11}$ pfu/ml, New England Biolabs, Inc.) were added to each well to facilitate the expression of scFv/phage.

Supernatants containing scFv/phage were harvested by centrifuging the plate at 1800×g for 5 min. The scFv/phage were then evaluated for targeting specificity in an ELISA assay using purified TEM7R ECD fusion on three individual ELISA plates (NUNC Maxisorp™), respectively.

One microgram of each protein in 1000 coating buffer (BupH™ carbonate-bicarbonate buffer) was applied to each well of the ELISA plates and incubated overnight at 4° C. The plates were then washed 3 times with PBS and blocked with 4% MPBS. 50 µl of each phage solution was mixed with an identical volume of in 4% MPBS containing 100 µg/ml IgG1 Fc, the solutions were incubated for 30 minutes at room temperature before adding to the individual ELISA wells. After a 2-3 h incubation at room temperature, the plates were washed sequentially 3 times with PBST and 3 times with PBS. Horseradish peroxidase conjugated mouse anti-phage antibody (Pharmacia) diluted 1:5000 with 2% MPBS was added (100 µl), incubated for 90 minute and then developed with substrate (HRP substrate Kit, Bio-Rad).

The ELISA plates were read on ELISA plate reader (Multiskan Ascent, Labsystems Ltd.) at 405 nm. Clones were considered to be positive for TEM7R ECD if their OD values in the ECD plates were greater or equal to 2.5 times the background OD, and they failed to bind to the control plate.

D. PCR Fingerprint and scFv Expression

Positive clones were picked from the Master plate and checked for the presence of scFv inserts by PCR using the primers LW743 (5'-GAA ATA CCT ATT GCC TAC G-3') (SEQ ID NO:1) and LW744 (5'-CTT ATT AGC GTT TGC CAT T-3') (SEQ ID NO:2). Unique colonies were identified using DNA fingerprinting with BstNI digestion of PCR amplification and automated sequencing (Marks, J D et al. (1991) J. Mol. Biol. 222:581-97).

To facilitate large-scale scFv production, the scFv-coding segments were cut using the NcoI and NotI restriction enzymes (New England Biolabs) and cloned into expression vector pUC119mycHis (Schier, R, et al. (1995) Immunotechnology 1:73-81). Soluble scFv were expressed in *E. coli* TG1, isolated from the periplasmic space and purified by Ni-NTA agarose affinity chromatography and high-performance liquid chromatography (HPLC) on a Superdex® 75 column (GE Healthcare) (Adams, G P et al. (1998) Cancer Res. 58:485-90). The size and integrity of the resulting scFv were assayed by 12% SDS-PAGE.

E. Physical Characterization of scFvs.

scFvs were expressed in *E. coli* and purified by sequential IMAC and size exclusion chromatography (Robinson, M K et al. (2005) Cancer Research 65:1471-8). Binding of the TEM7R scFv, to extracellular domain (ECDs) was characterized by SPR using TEM7R ECD as the target antigen (Yuan, Q A et al. (2006) Mol. Cancer. Ther. 5:2096-105). ECD was diluted to 10 µg/mL in 10 mM sodium acetate pH 5.2 and approximately 200 RU of ECD were immobilized onto CM5 sensor chips via NHS-ester chemistry.

Kinetic constants for A5 were determined by passing serially diluted samples (0 nM to 2 µM) over flow cells at flow rate of 40 µL/min. Response against an ErbB2 coated flow cell was used as a negative control and subtracted from the response generated against the TEM7R ECD to obtain the final sensorgrams. Data was evaluated using BIAEvaluation 3.2 software (BIAcore, Piscataway, N.J.) and fit using the 1:1 Langmuir binding model. Flow cells were regenerated by sequential 15-second pulses with 10 mM glycine, pH 2 and 50 mM Triethylamine, pH 10 followed by equilibration with PBS running buffer.

F. IgG Construction.

To establish the location of the target antigen in the tumor xenografts, scFv#4 was converted into a IgG1 format. Mammalian vector pMAZ-IgH for human γ1 heavy chain expression and pMAZ-IgL for human K light chain expression were designed by Dr. Itai Benhar (gift of Dr. Benhar, Tel-Aviv University) for the production of human IgG1 antibodies in mammalian cell culture. The resultant IgG1 antibodies were named BB1.

The IgH plasmid carries a neomycin expression cassette for genetamycin (G418) selection, while the IgL plasmid carries a hygromycin B resistance cassette for the isolation of stable transfectants under double drug selection. The VH region of the scFv was amplified using primers that were designed to introducing BssHII site at the 5' end and a NheI restriction site at the 3' end. The PCR product was inserted into plasmid pMAZ-IgH via the BssHII/NheI sites. The VL region was amplified using primers designed to introduce BssHII site at the 5' end and a BsiWI restriction site at the 3' end. The PCR product was inserted into plasmid pMAZ-IgH via the BssHII/BsiWI sites.

The expressed constructs were sequenced and found to be in correlation agreement with the original scFv and in frame with the pMAZ plasmid sequence. Co-transfection of HEK293 cells with pMAZ-IgH and pMAZ-IgL expression was performed using the nonliposomal transfection reagent FuGENE® 6 (Fugent, LLC) according to the manufacturer's instruction. 1.2 mg/ml G418 and 200 mg/ml hygromycin B were used for selection. Cells were diluted to be grown as separate colonies.

The resulting plasmids were co-transfected into CHO cells and the resulting IgG (BB1) was purified by Protein A affinity chromatography with typical yields of 1.5 mg/L of culture supernatant.

The single chain antibody does not have any immune effector cell binding ability, and cannot induce ADCC (antibody dependent cellular cytotoxicity). The size of the scFv is in the order of about 25 kD, and the size of the BB1 IgG is about 150 kD.

G. Biodistribution Studies.

SCID mice were implanted subcutaneously with five tumor cell lines of varying origin and targeting of labeled scFv#4 was assessed by biodistribution and positron emission tomography (PET) imaging (Adams, G P et al. (1993) Cancer Res. 53:4026-4034). In brief, mTEM7R scFv #4 and a control scFv (C6.5, Anti-Her2/neu) that targets the HER2/neu ECD were labeled with $^{125}$I ($^{124}$I for PET studies) to a specific activity of ~1 µCi/µg and were confirmed to have retained the ability to bind to their respective target antigens in live cell binding assays.

The radiolabeled scFv molecules were administered to mice by intravenous tail vein injection (20 µg/mouse) once xenografts had reached 100-300 mg (n≥5/tumor type/time point). At specific time points thereafter, animals were euthanized, dissected, and tumors, blood and normal organs were weighed and counted to determine the percent injected dose/gram tissue and tumor:normal organ ratios.

H. Immunohistochemical Staining.

Quick snap frozen tumor tissues were embedded in OCT freezing solution (Tissue-Tek) and stored at −80° C. before sectioning with a cryostat. Frozen sections (10 µm) were washed with PBST (PBS+0.05% Tween® 20 (ICI Americas, Inc.)) and fixed in cold acetone for 10 min. Tissue sections were treated with 0.3% hydrogen peroxide in PBS for 15 min to block endogenous peroxidase activity and blocked with 3% bovine serum albumin in PBS to minimize background reactivity. Primary antibodies, human-anti TEM7R antibody (BB1) or rat-anti mouse CD31 monoclonal antibody (BD Sciences), were applied at 1:10 dilution for overnight at 4° C. After washed with PBST, amplification and development by BioGenex (San Ramon, Calif.) biotin-streptavidin detection system with horseradish peroxidase were followed by manufacturer's directions.

I. Immunofluorescence.

To detect the co-localization of BB1 and CD31 expression, BB1 and CD31 double staining was performed in tumor tissues from xenografted mice or BB1 injected mice. The preparation and sectioning of frozen tissues were processed as described above. The secondary antibodies of goat-anti human IgG (H+L) Alexa Fluor® 488 (Molecular Probes, Inc.) for BB1 and goat-anti-rat IgG (H+L) Alexa Fluor® 594 (Molecular Probes, Inc.) for CD31 were applied to the samples for 1 hr at room temperature. Nuclear staining was performed with DAPI (Invitrogen) for 10 min at room temperature. Samples were mounted with fluorescent mounting media (Prolong Gold antifade reagent, Invitrogen). Images were obtained with an Optical Apparatus fluorescence microscope.

J. Flow Cytometry.

Briefly, BB1 IgG was incubated with $5\times10^5$ cells at 4° C. in PBS containing 1% FBS to establish equilibrium. The cells were washed twice with PBS and 100 microliters (1 microgram/ml) of PE-labeled anti-human Fc was added. After 30 minutes at 4° C., the cells were washed twice and resuspended in PBS containing 4% paraformaldehyde. Bound IgG was detected by flow cytometry in a FACS LSRII (Becton Dickinson), and median fluorescence intensity (MFI) was calculated using Cellquest™ software (Becton Dickinson).

K. Internalization Assays.

Hum-ZAP cytotoxicity assay (Advanced Targeting System, San Diego, Calif., USA) was used for these assays. This assay system takes advantage of the cell killing ability of a toxin, saporin, that is conjugated to a secondary antibody capable of binding to any IgG. Once internalized, the toxin is released resulting in cell death.

Internalization of BB1 was tested in F9 mouse embryonic carcinoma cell line using a secondary antibody conjugate (Hum-ZAP). The cytotoxicity assay was performed on a five-day timetable.

F9 cells (5000 cells/well) were seeded to a 96-well plate in 90 μL of 2% DMEM/HEPES media on Day 1. On Day 2, 10 μL of either the antibody alone or combination of the antibody with Hum-ZAP or control agents were added to the wells. Following a 3 day incubation period (on Day 5), cell proliferation was measured using a Perkin Elmer Envision Plate reader after a 2 hour incubation with 10 μL of alamarBlue per well.

The assay was carried out as follows: (1) Cisplatin (positive control); (2) BB1; (3) BB1+Hum-ZAP; (4) Rituximab (negative control); (5) Rituximab+Hum-ZAP; (6) Hum-ZAP only. There were four concentrations used for each condition (with exception of Hum-ZAP only); these concentrations were: (1) 0.2 mg/mL; (2) 0.1 mg/mL; (3) 0.05 mg/mL; and (4) 0.025 mg/mL. In total, there were three replicates for each treatment at each concentration.

L. Matrigel Plug Assay In vivo.

Matrigel® (Discovery Labware, Inc., Bedford, Mass.) mixture (0.5 ml) containing F9 cells or F9 cells plus antibodies were injected subcutaneously in the flank regions of SCID mice. For the antibodies group, 500 μg of anti-TEM7R (BB1) or Avastin® (Bevacizumab) (Genentech, Inc., San Francisco, Calif.) were incubated with $1\times10^6$ F9 on ice for 10 minutes before mixing with matrigel. Two control groups were injected with F9 cells or Matrigel® only. Matrigel® plugs were excised at 7 and 14 days after implantation, photographed, and processed for histological studies. The vascularization of Matrigel® plugs were visualized by H.E. and anti-mouse CD31 staining.

Example 2

Experimental Results

A. Isolation of TEM7R Reactive Antibodies from a Naïve Human Phage Display Library.

A naïve human scFv phage display library comprised of $10^{10}$ independent clones was used to isolate scFv molecules reactive with mTEM7R. Using a solid phase panning strategy, 5 families of anti-TEM7R scFv were identified based on fingerprint analysis. A representative from each family was subcloned into the pSYN2 expression plasmid, transformed into TG1 E. coli, expressed, and purified from the periplasmic space using standard techniques (Adams, G P et al. (1999) J. Immunol. Methods 231:249-60). Of the 5 families of scFv, 2 families specifically bound to the mTEM7R ECD as confirmed by surface plasmon resonance (SPR) on the BIAcore and by ELISA (Schier, R et al. (1995) Immunotechnology 1:73-81; and, Schier, R et al. (1996) J. Mol. Biol. 263:551-567). Clone 4 (scFv#4) exhibited higher affinity for purified ECD (10-8 M) as measured by SPR (FIGS. 1a-1e) and was chosen for further studies.

B. Anti-mTEM7R scFv#4 Selectively Targets Tumors In Vivo.

Figure 3:
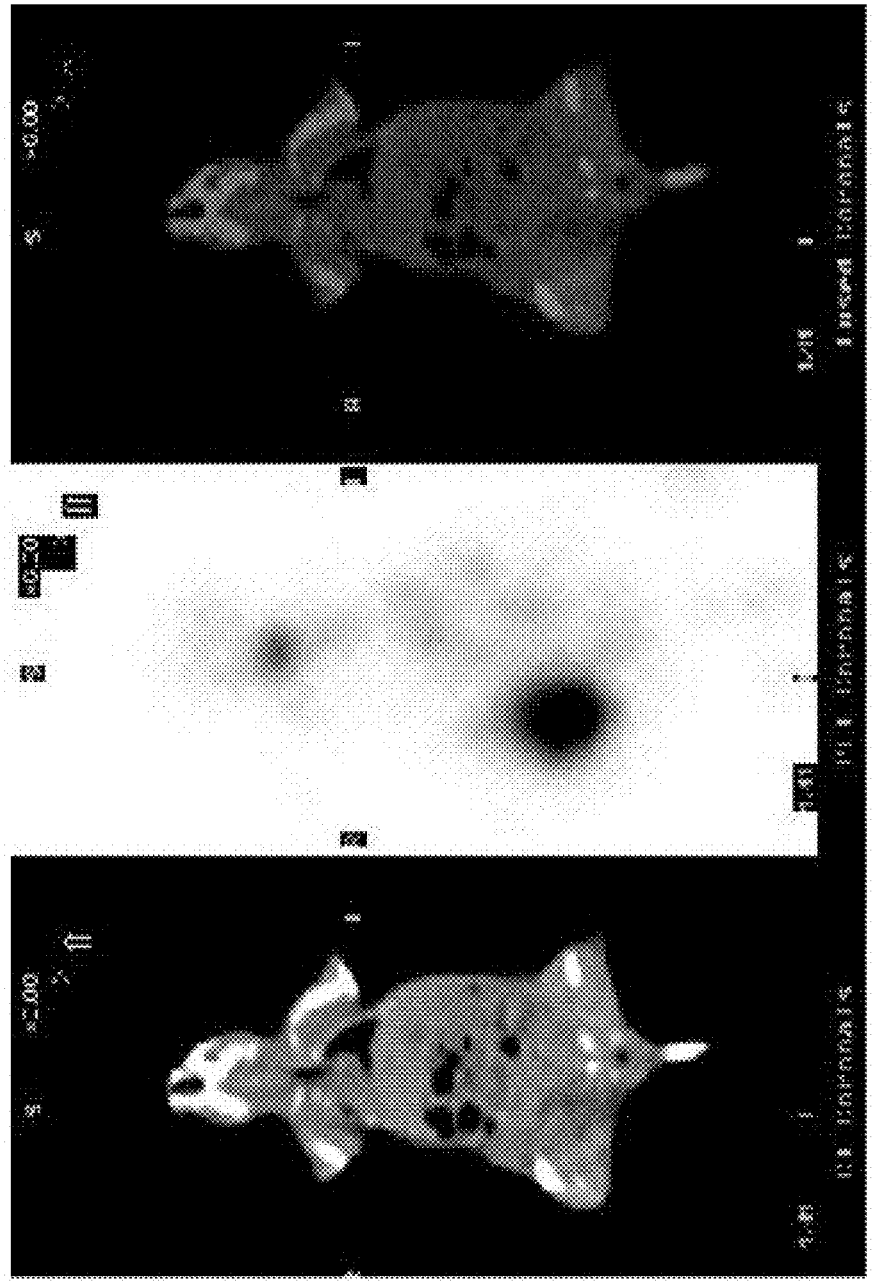
FIG. 3 shows a representative Positron Emission (PET) image. A mouse with A431 xenograft was injected with $^{124}I$ labeled scFv#4, and the picture was taken 72 hours post injection.
Figure 4:
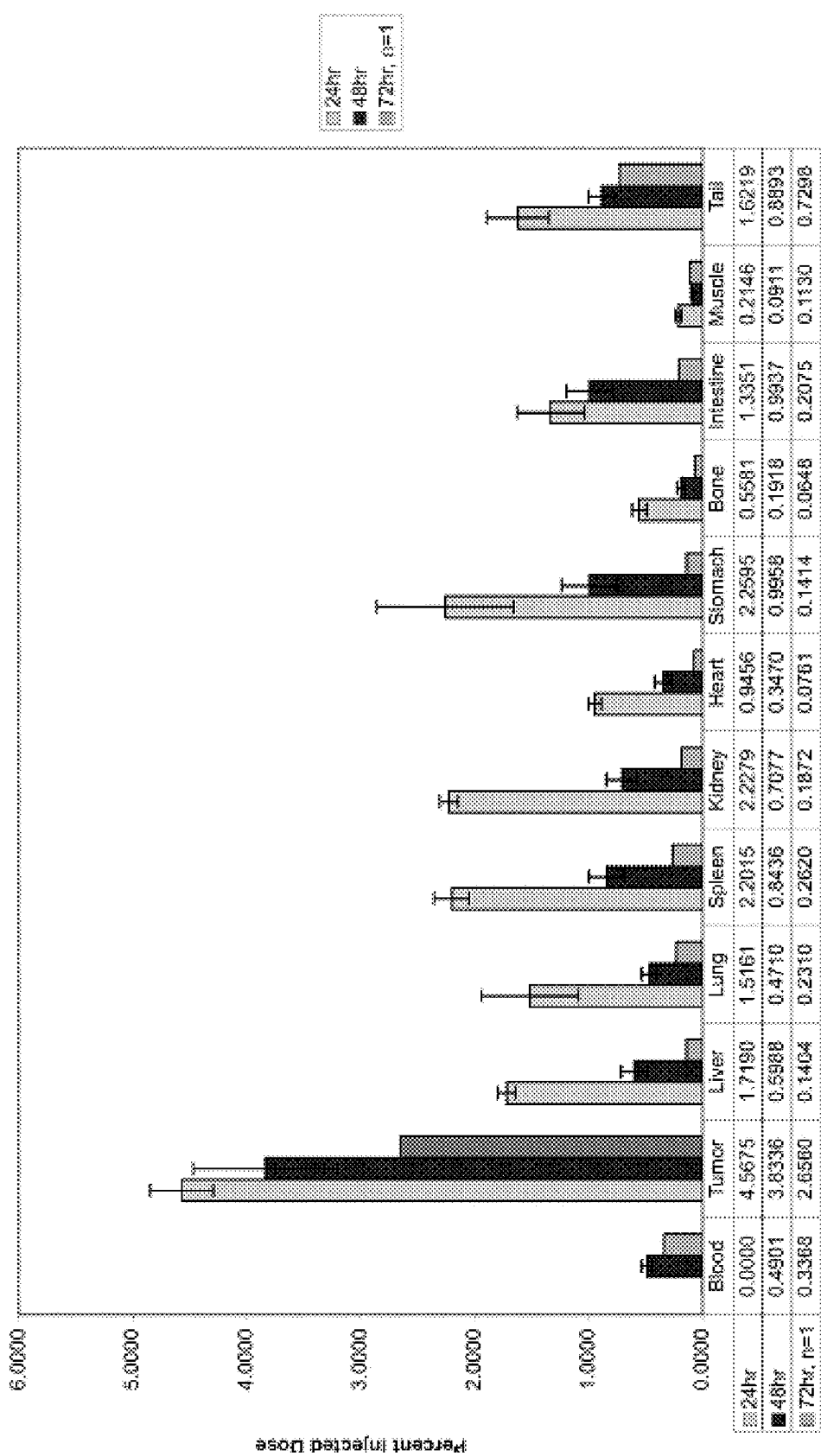
FIG. 4 shows results of a biodistribution study with $^{124}I$ as part of the PET imaging study shown in FIG. 3.

TEM7R is overexpressed on tumor vasculature and therefore scFv#4 should selectively target tumor xenografts in a SCID mouse model. Biodistribution of scFv#4 at 24 hours displayed significantly higher retention in tumor than is typically achieved with scFv molecules targeting a tumor surface antigen (2 to 3.4% ID/g, FIG. 2A). By comparison, C6.5 scFv in HER2/neu positive xenografts (FIG. 2B) is typically less than 1% ID/g 24 hours following intravenous injection. However, the most interesting observation was that the selective tumor retention of scFv#4 persisted over a prolonged period of time. At 72 hours, tumor uptake remained at 2.6% ID/g with tumor:organ ratios exceeding 10:1. This selective persistence of the labeled scFv is highlighted in the PET image in FIG. 3. During these PET image study, biodistribution of 1241 scFv was evaluated in various tumors over a 72 hour period, and these results are shown in FIG. 4.

C. Anti-mTEM7R Localizes to the Tumor Vasculature.

Figure 5:
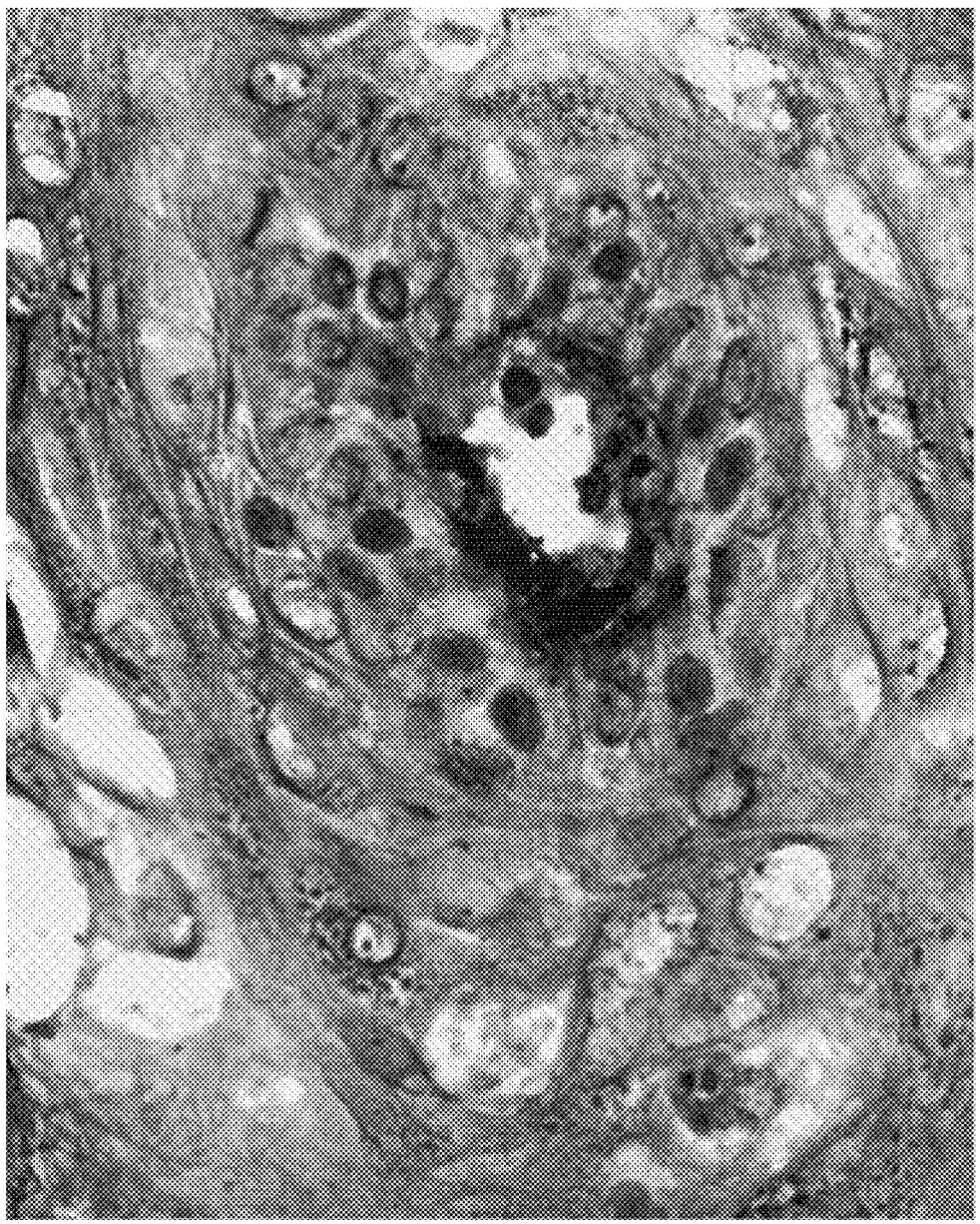
FIG. 5 shows immunohistochemistry with A431 xenografts to localize TEM7R with BB1 (scFv#4 expressed in human IgG1 form). Mice were treated with BB1 and tumors resected 24 hours post injection. Secondary staining with anti-human IgG was carried out. Dark staining shows localization of the antibody to TEM7R.
Figure 6:
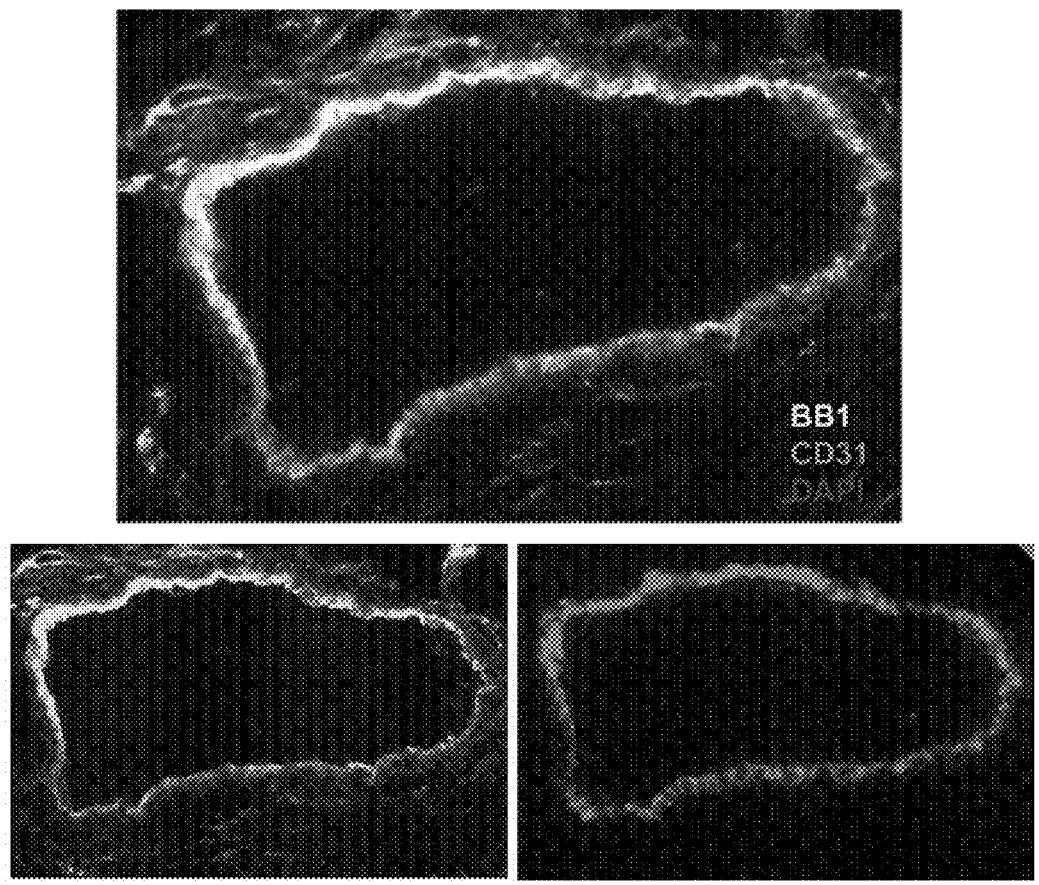
FIG. 6 shows the results of immunofluorescence studies, carried out using the same conditions as the experiments shown in FIG. 3. The bottom left panel shows the staining of BB1, and the bottom right panel shows the staining of CD31. The top panel shows co-expression.

Although scFv#4 displayed promising tumor targeting in biodistribution and imaging studies described above, these studies did not address the hypothesis that the scFv targets the tumor vasculature as compared to the tumor cell surface. IHC and IF were performed on fresh-frozen samples to investigate tissue distribution. FIG. 5 shows a representative blood vessel from an A431 xenograft vessel post injection with BB1. Co-localization of TEM7R with CD31 was confirmed by immunofluorescence. FIG. 6 shows a representative image that confirms binding to CD31-expressing endothelium in tumor xenografts.

Figure 7:
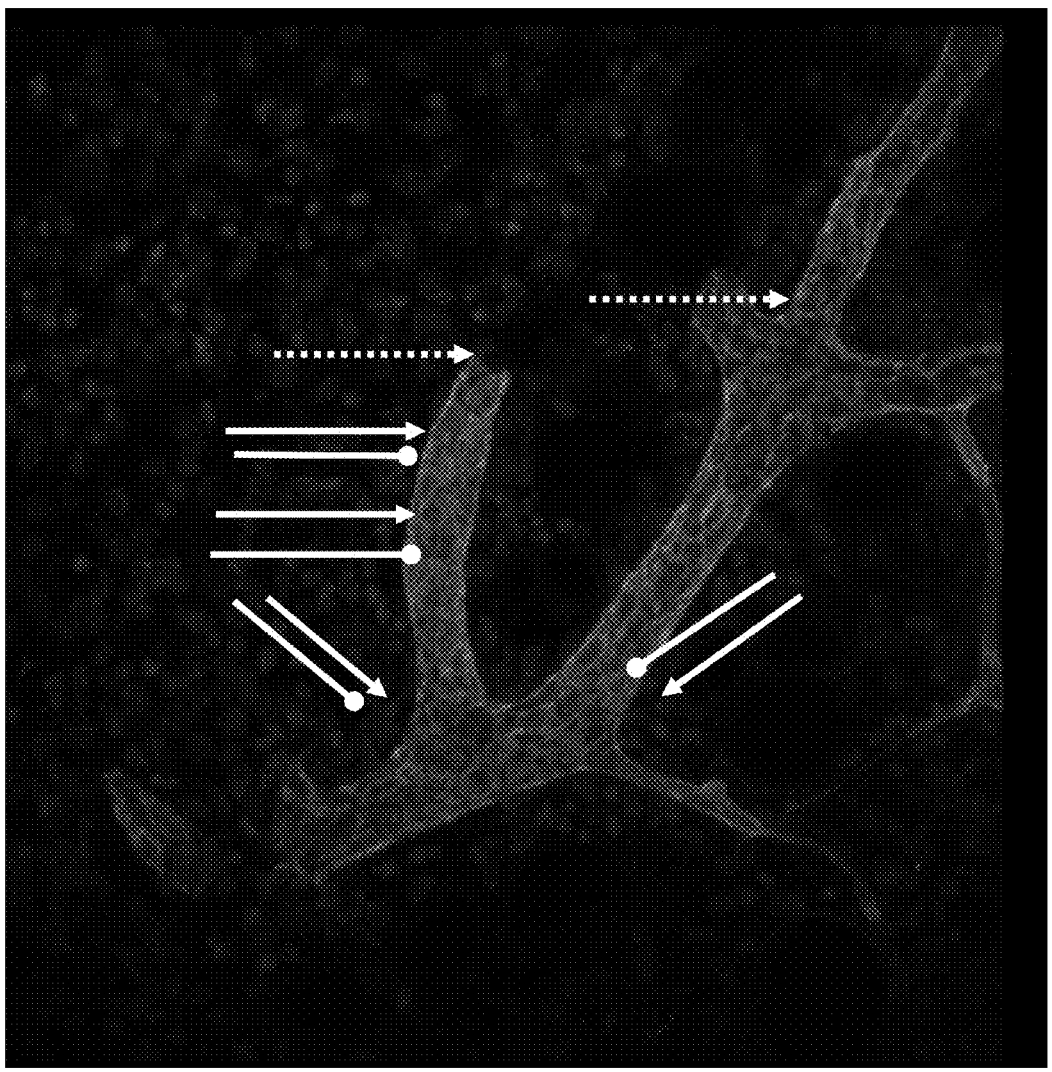
FIG. 7 shows an image from a tumor associated blood vessel that shows co-localization of the TEM7R IgG antibody BB1 and vascular endothelium marker CD31 (CD31 arrows have rounded heads and BB1 arrows have pointed heads with a solid line; DAPI staining is shown with arrows having dashed lines).

A431 tumors were grown to a palpable size in SCID mice. Tumors were excised and immunofluorescence staining was performed using the IgG anti-TEM7R antibody BB1; CD31 was used as a marker for vascular endothelium (stained with anti-CD31 antibodies. FIG. 7 shows an image from an excised tumor's associated blood vessel, and demonstrates colocalization of BB1 and CD31 (round arrow is CD31 and pointed arrow is BB1, dashed line arrow is DAPI). These results suggest that the target of BB1, TEM7R, is in the vascular endothelium and colocalizes with CD31, a commonly used marker for vasculature.

Figure 8:
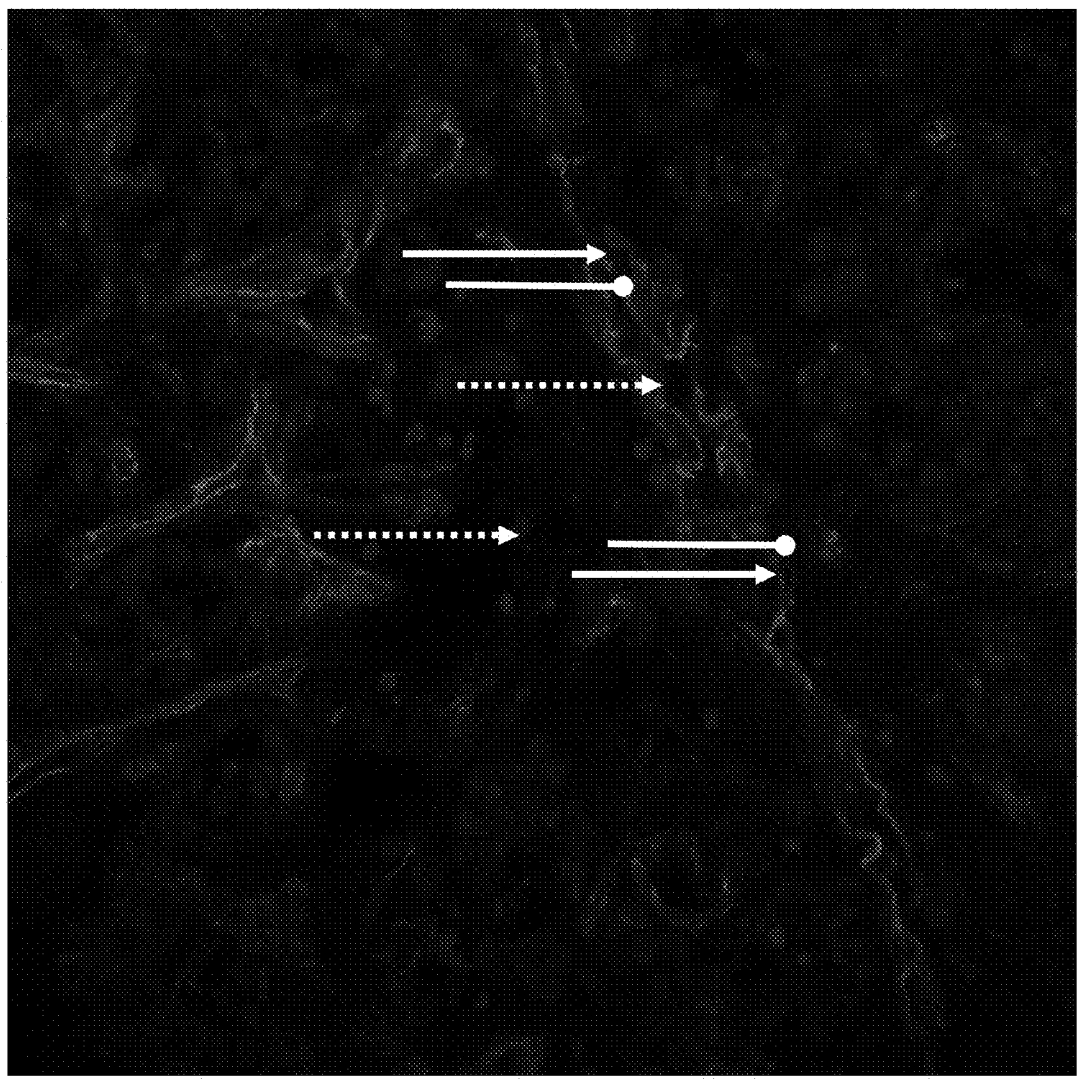
FIG. 8 shows an image of F9 teratocarcinoma tumors in SCID mice labeled with antibodies to CD31 and the TEM7R IgG antibody BB1, excised from the mice and subject to immunofluorescence. CD31 (round head arrows) and BB1 (pointed head arrows with a solid line) co-localize to the vascular endothelium. DAPI staining is shown with arrows having dashed lines.

F9 teratocarcinoma tumors were grown to a palpable size in SCID mice. Tumors were excised and immunofluorescence staining was performed as described above for the A431 tumors. FIG. 8 shows an image from an excised tumor's associated blood vessel, and demonstrates colocalization of BB1 and CD31 (round arrow is CD31 and pointed arrow is BB1, dashed line arrow is DAPI).

D. Anti-TEM7R IgG Binds Human and Mouse TEM7R by Flow Cytometry

Figure 9:
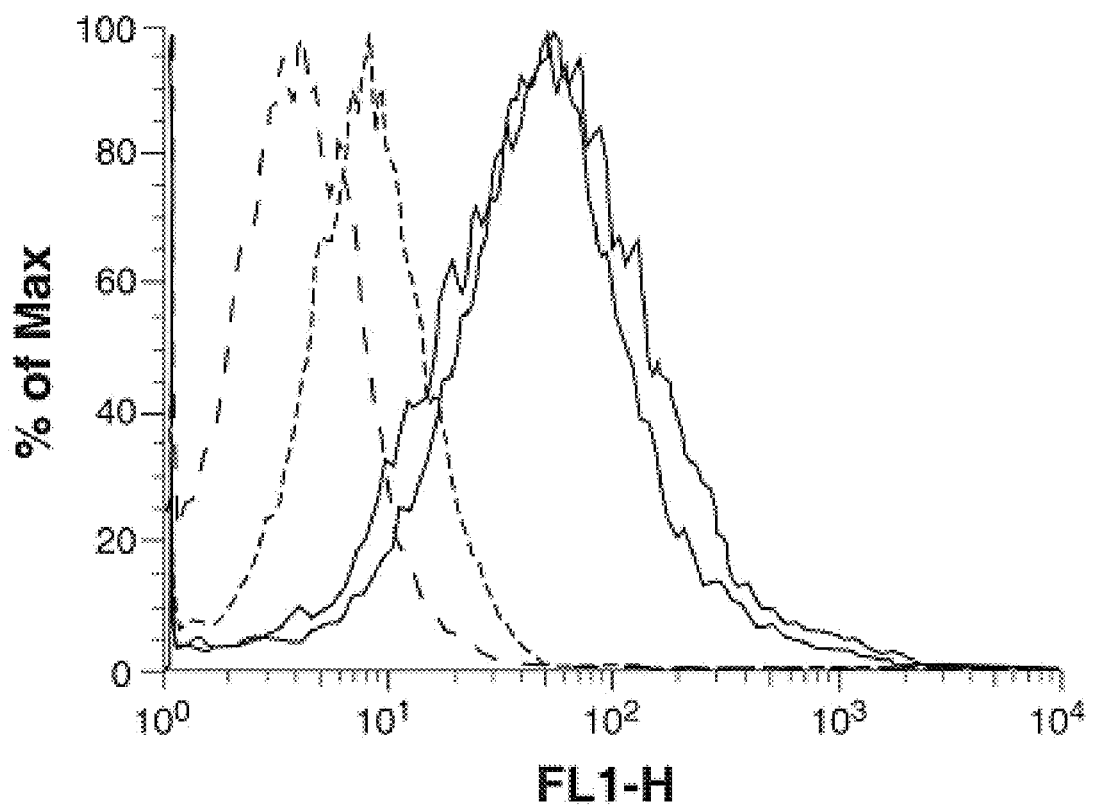
FIG. 9 shows mouse TEM7R expression by cos-7 cells. Flow cytometry studies showed binding of BB1 supernatant (CHO cell culture making the antibody) as the source of antibody against TEM7R (lightest gray, right-most edge of graph is the second line from the right of the chart) and purified TEM7R antibody (middle gray, right most edge of graph is the first line from the right of the chart). The first graph (darker gray, left edge of graph) shows cells alone, and the second graph (darkest gray) shows cells with secondary antibody alone as a control.

The extracellular domain of murine and human TEM7R was expressed in pDisplay plasmid (Invitrogen) by standard methods. pDisplay is a mammalian expression vector that is designed to target and anchor recombinant proteins on the cell surface using the N-terminal cell surface targeting signal and the C-terminal transmembrane anchoring domain from a platelet derived growth factor receptor. Briefly, the TEM7R ECD gene, previously cloned, was excised and ligated into the pDisplay vector. After sequence confirmation, transient transfection of COS-7 cells was carried out with the appropriate plasmids. The anti-TEM7R IgG (BB1) shows excellent binding to the ECD of both human (FIG. 10) and murine TEM7R (FIG. 9).

E. Matrigel® Assays with BB1.

Figure 11A:
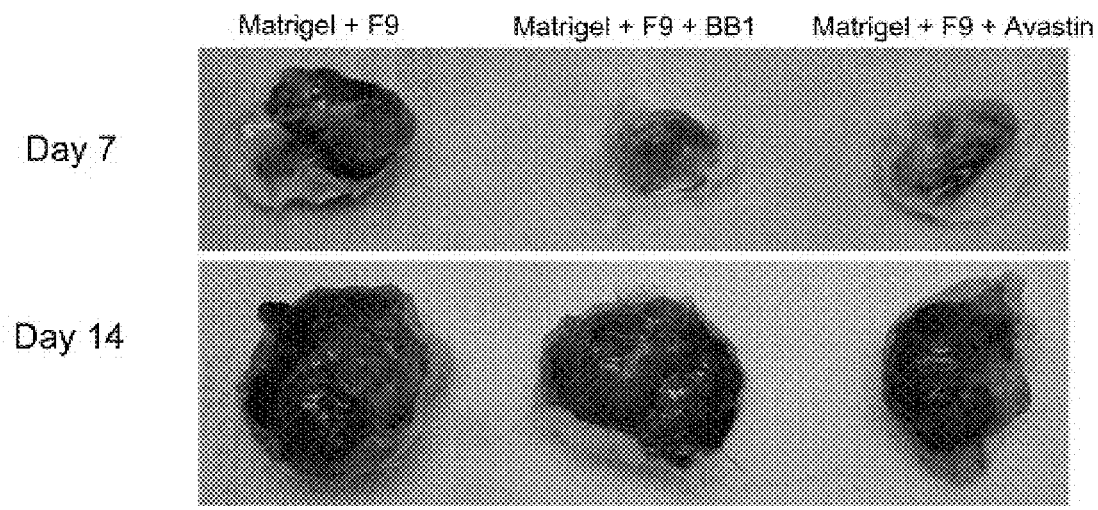
FIG. 11a shows a photograph of tumors removed from mice: Matrigel® (250 µl)+F9 cells (1 million)+ or −500 µg TEM7R IgG antibody BB1 (Avastin® was used as a control) were preincubated with F9 cells for 10 min on ice before mixing with Matrigel®.
Figure 11B:
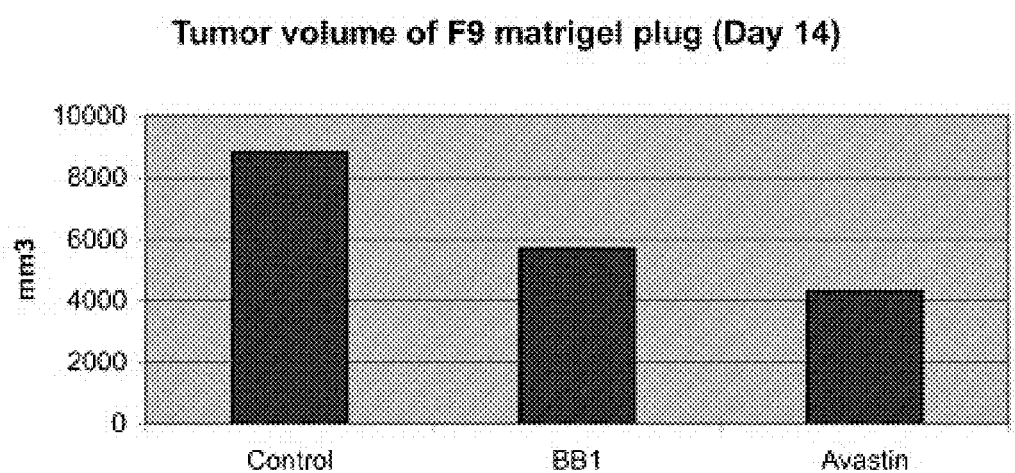
FIG. 11b shows the measurements of the tumors in FIG. 11a graphically. Control tumors (no TEM7R antibody) are about 50% larger than tumors treated with the BB1 antibody (center)

Matrigel® (Discovery Labware, Inc., Bedford, Mass.) in a volume of 250 µl was mixed with 1 million F9 teratocarcinoma cells +/−500 µg of BB1 anti-TEM7R antibody or Bevacizumab (Avastin®; Genentech, Inc., San Francisco, Calif.) control. Bevacizumab was used as a control antibody because of its known anti-vascular properties. The antibodies were preincubated with the F9 cells for 10 minutes on ice before mixing with the Matrigel®. The Matrigel® mixture was then placed into a mouse and allowed to grow. After a specified period of time (7 or 14 days), the Matrigel® tumors were removed and the tumors were measured. FIG. 11a shows a photograph of the actual Matrigel®/tumors removed from the mice at day 7 or day 14. FIG. 11b shows a bar graph of the measurements of the tumors shown in FIG. 11a in cubic millimeters. The results show that treatment of the tumors with the BB1 antibody was as effective as the Avastin® positive control antibody. Negative control tumors (not treated with any antibody) are about 50% larger than their antibody-treated counterparts.

Figure 12A:
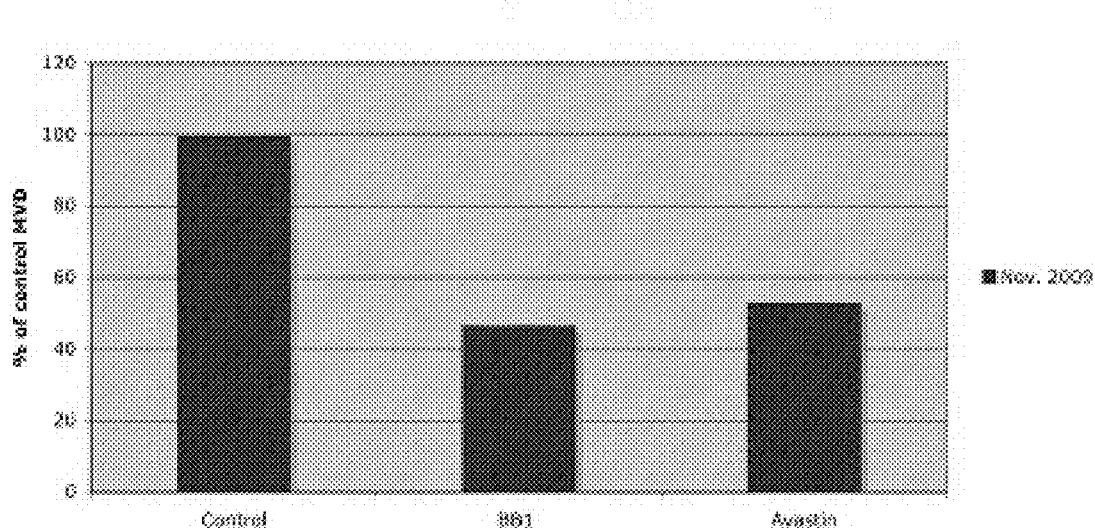
FIGS. 12a and 12b show the average number of blood vessels per field of each tumor in control (untreated) versus BB1-treated and Avastin®-treated tumors.
Figure 12B:
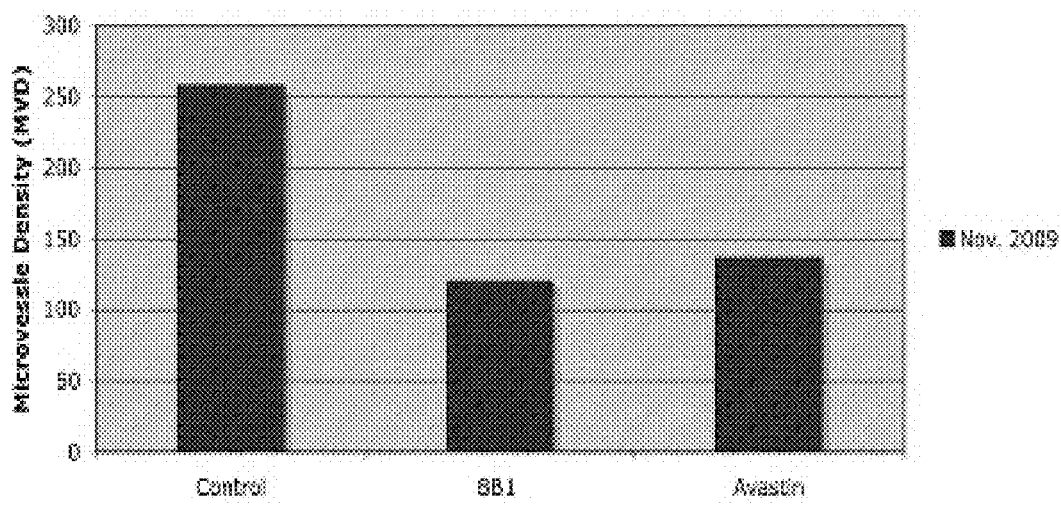

Tumors were then evaluated for blood vessel formation. The number of blood vessels per field in each tumor was counted and the average was calculated. The results are shown in FIGS. 12a and 12b. FIG. 12a shows the % of blood vessels in the BB1 and Avastin®-treated tumors relative to controls. FIG. 12b shows the microvessel density (MVD) of control and BB1 and Avastin®-treated cells.

Figure 13A:
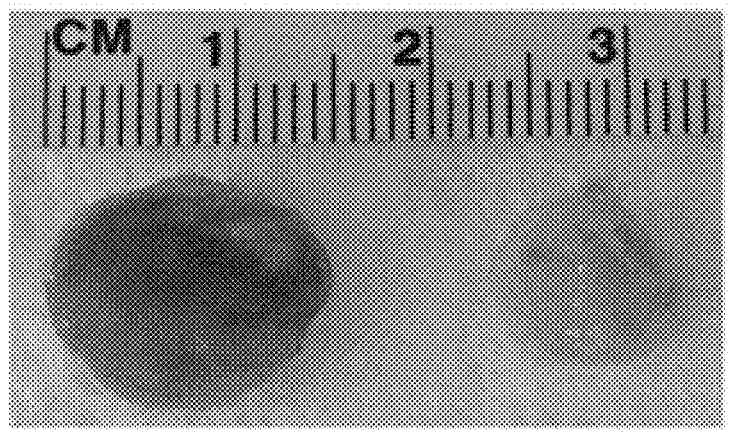
FIG. 13a shows the results of a second Matrigel® experiment for tumor size.
Figure 13B:
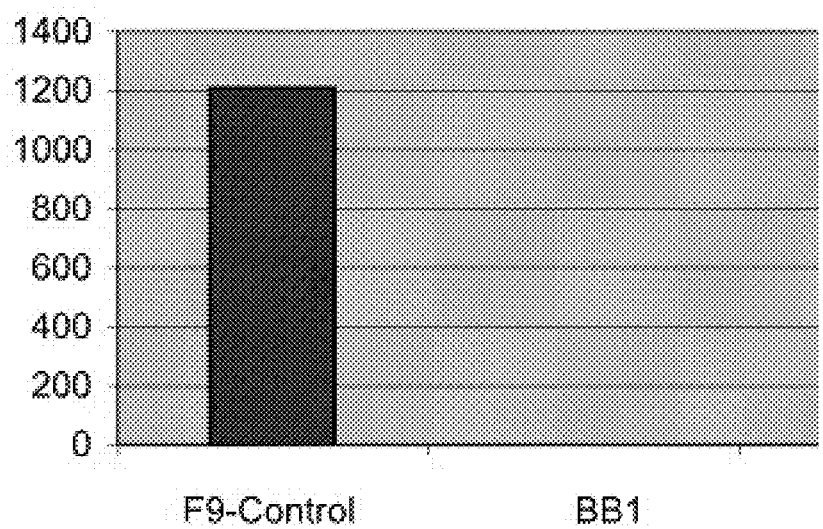
FIG. 13b shows the size of the Matrigel® plug in the control (left bar) and BB1-treated (right bar) tumors. The treated tumor is almost completely gone.

The F9 Matrigel® experiment was repeated, and the results of this experiment are shown in FIG. 13. FIG. 13a shows a photograph comparing F9 control tumors and BB1-treated F9 tumors side-by-side with a ruler showing approximate sizes in centimeters. FIG. 13b shows the size of each Matrigel® plug in cubic millimeters. The F9 control is about 1200 mm$^3$, and the BB1-treated tumor is almost completely gone.

Figure 14A:
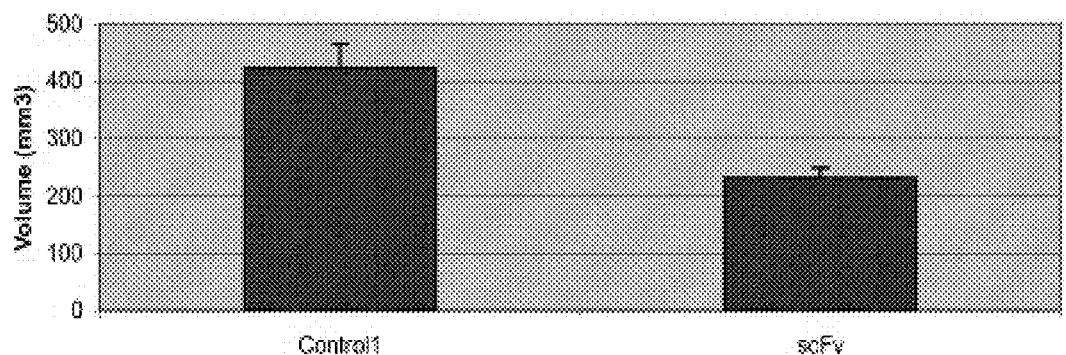
FIG. 14a shows the results of a Matrigel® experiment carried out using the anti-TEM7R scFv (scFv#4) on A431 (epidermoid carcinoma) cells.
Figure 14B:
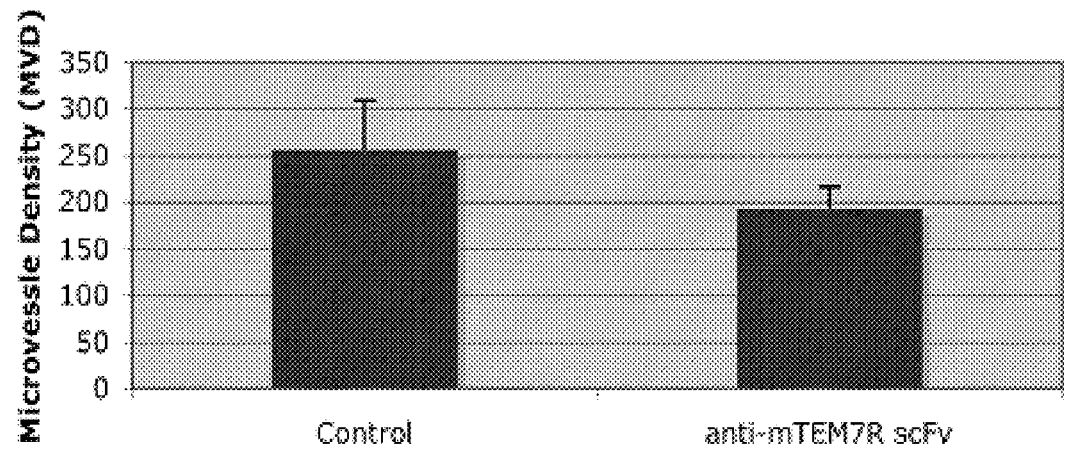
FIG. 14b shows the results of a microvessel density experiment carried out using the scFv.
Figure 15A:
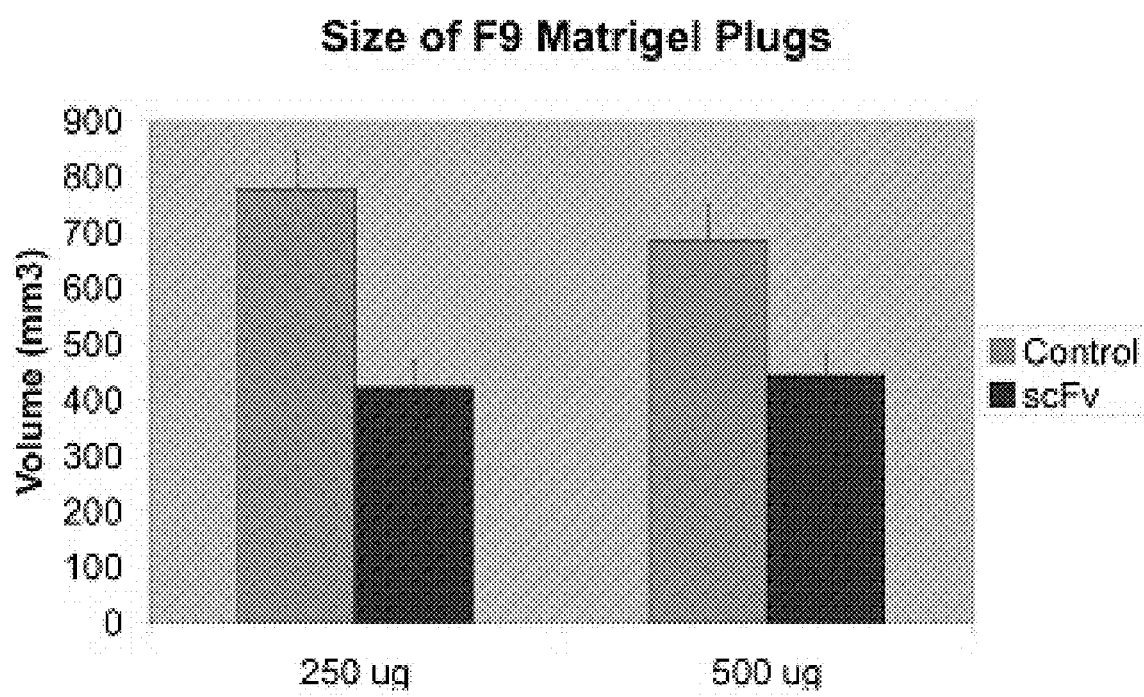
FIG. 15a shows the results of a Matrigel® experiment carried out using the anti-TEM7R scFv (scFv#4) on F9 teratocarcinoma tumors.
Figure 15B:
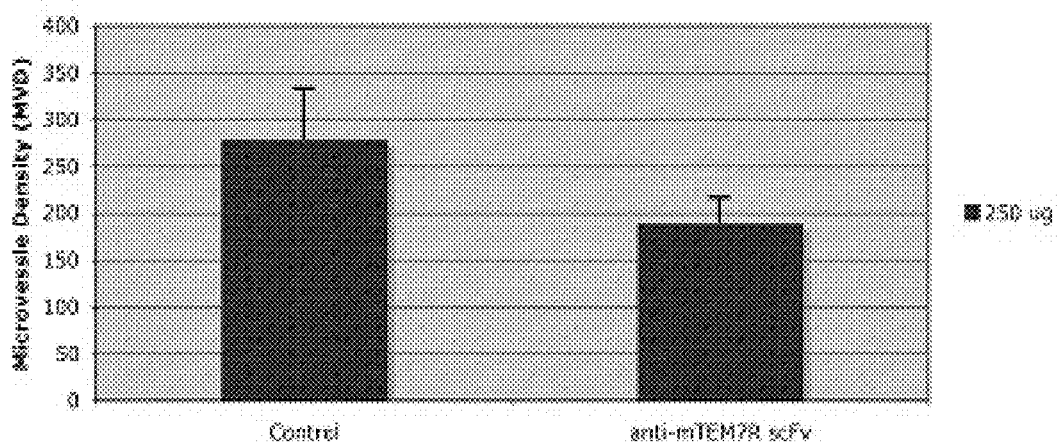
FIG. 15b shows the results of a microvessel density experiment carried out using the scFv at 250 µg of scFv.
Figure 15C:
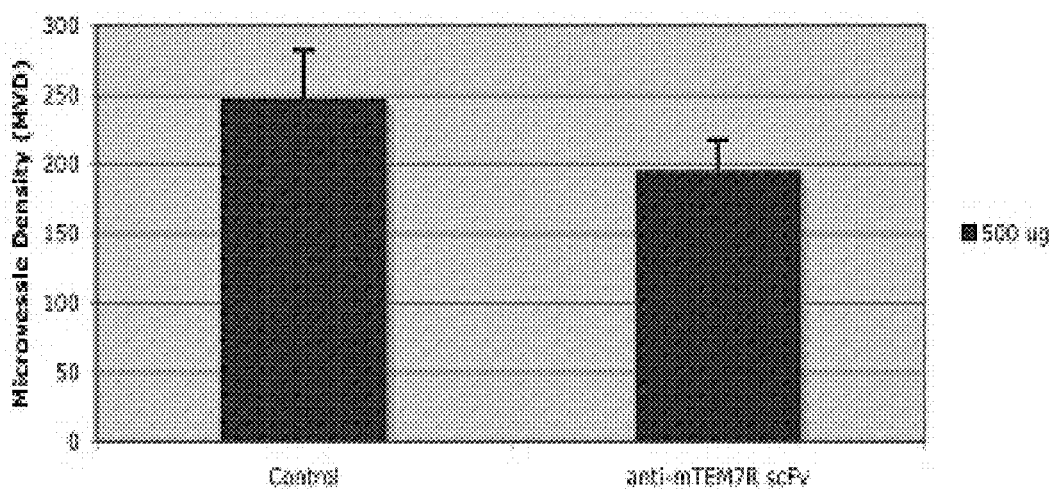
FIG. 15c shows the results of a microvessel density experiment carried out using the scFv at 500 µg of scFv.

Similar Matrigel® experiments were carried out using the anti-TEM7R scFv. FIG. 14a shows the volume of the Matrigel® plug impregnated with A431 tumor cells following treatment with the scFv or no-antibody controls (left bar). FIG. 14b shows the microvessel density (MVD) for each Matrigel®-A431 plug; n=4. FIG. 15a shows a separate experiment using F9 teratocarcinoma cells treated with different concentrations of the scFv and the control (no antibody). FIG. 15b shows the microvessel density (MVD) for the Matrigel® plug treated with 250 µg of scFv; n=3. FIG. 15c shows the MVD for the Matrigel® plug treated with 500 µg of scFv; n=2. Error bars indicate the average of all tumors.

F. Internalization Assay

Figure 10:
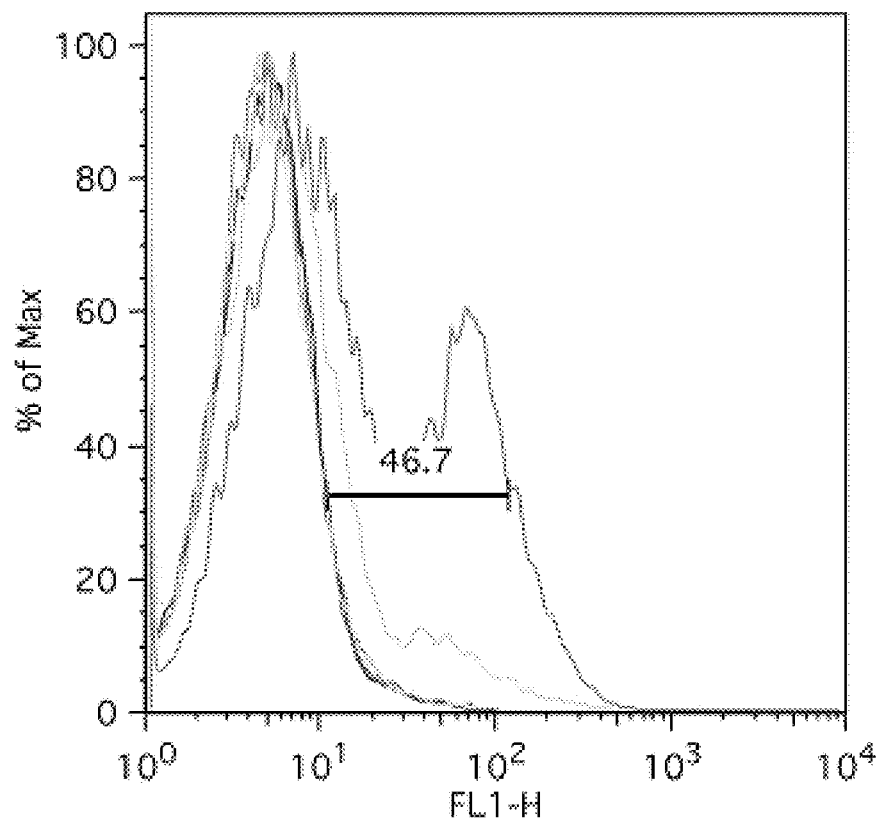
FIG. 10 shows results of a flow cytometry study of Human TEM7R with purified BB1. The value 46.7 refers to the mean fluorescence shift compare to baseline.
Figure 16:
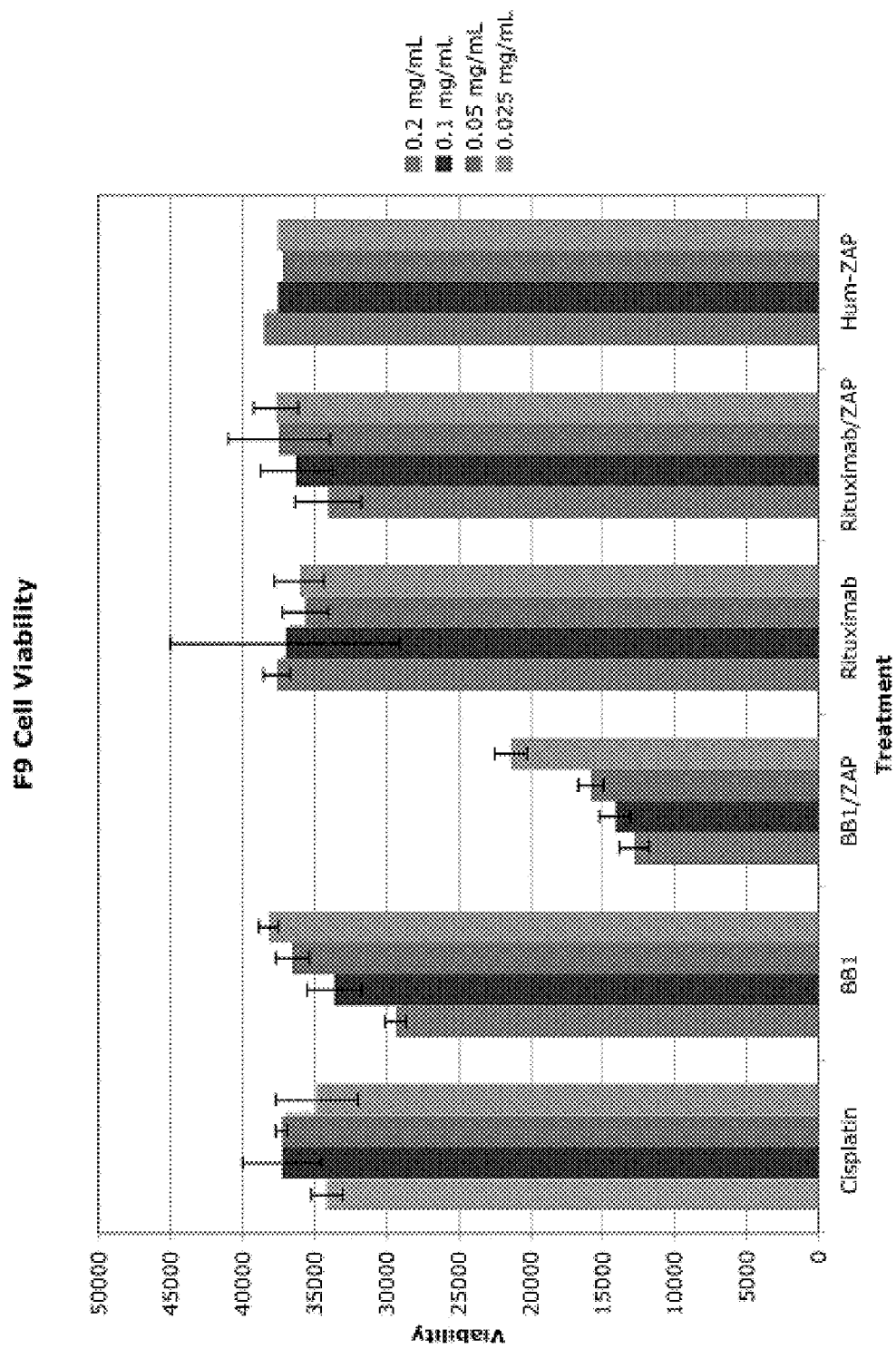
FIG. 16 shows viability of F9 cells treated with a chemotherapeutic agent, anti-TEM7R antibody BB1, or agent-antibody conjugates in an internalization assay. The bars moving from left to right in each group on the chart are concentrations at 0.2 mg/ml, 0.1 mg/ml, 0.05 mg/ml, and 0.025 mg/ml.

As shown in FIG. 16, BB1 is internalized by F9 cells. Cisplatin was used as an example of a chemotherapeutic agent with potential activity in this cell line. Rituximab was used as a negative control since F9 cells are not known to have CD20 (target of rituximab) expression. As shown in FIG. 10, the combination of BB1 conjugated with the secondary antibody had the highest level of cell killing suggesting internalization of the antibody-toxin conjugate.

G. Tumor Growth In Vivo.

Figure 17:
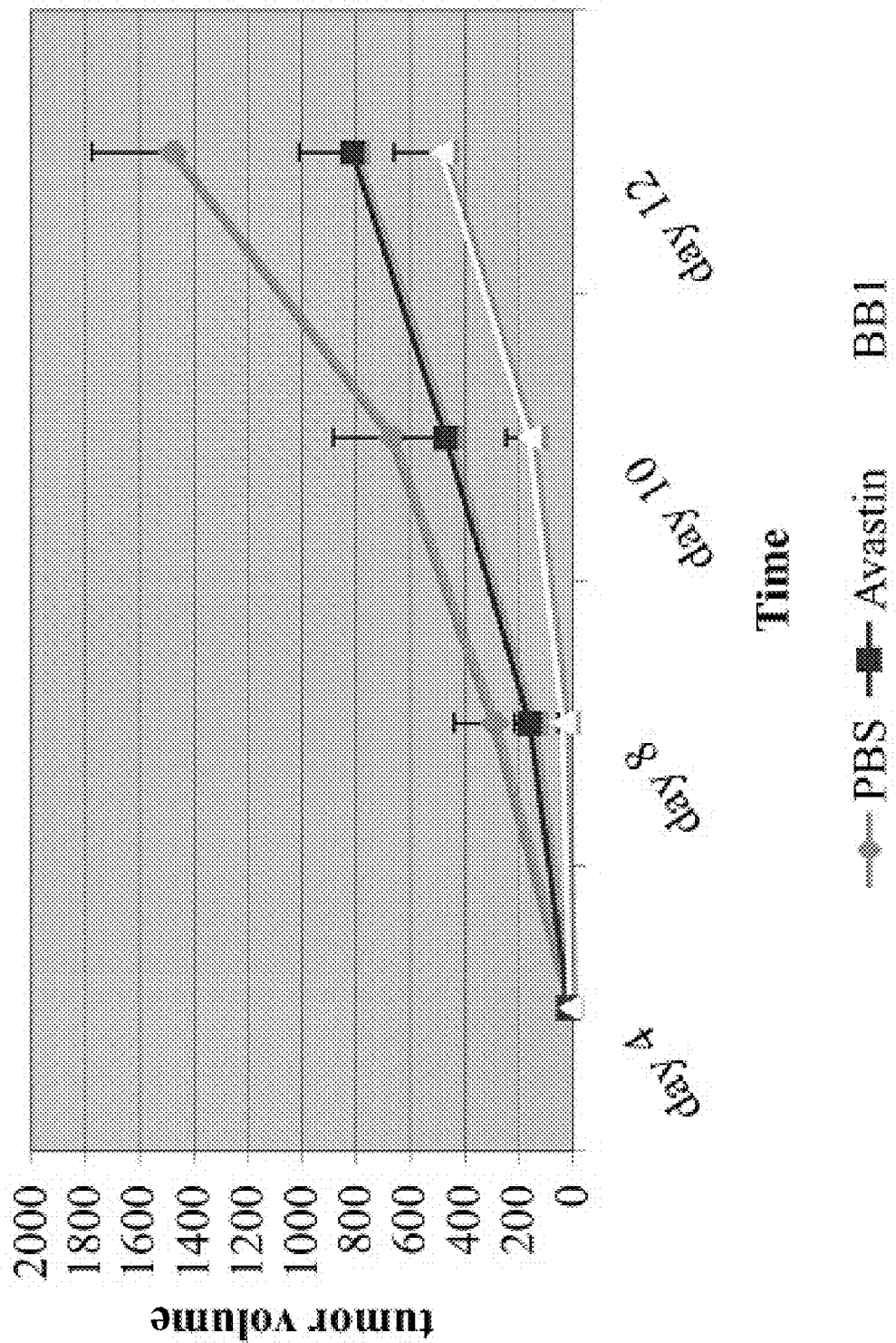
FIG. 17 shows results of in vivo experiments on mice having F9 teratocarcinoma tumor xenografts. After two weeks, mice treated with BB1 (triangles) had smaller tumors relative to mice treated with a PBS control (diamonds) or Avastin® control (squares).

F9 teratocarcinoma tumors were xenografted into nude mice (5 per group). Control mice were treated with phosphate buffered saline (PBS). One group of mice were treated with BB1 antibodies, and another group of mice were treated with Avastin.® Mice were followed for antibody efficacy and toxicity over a two week period. As shown in FIG. 17, BB1-treated mice (triangles) had significantly smaller tumors relative to PBS-control mice (diamonds) and Avastin®-treated mice (squares).

Example 3

Discussion

Figure 2A:
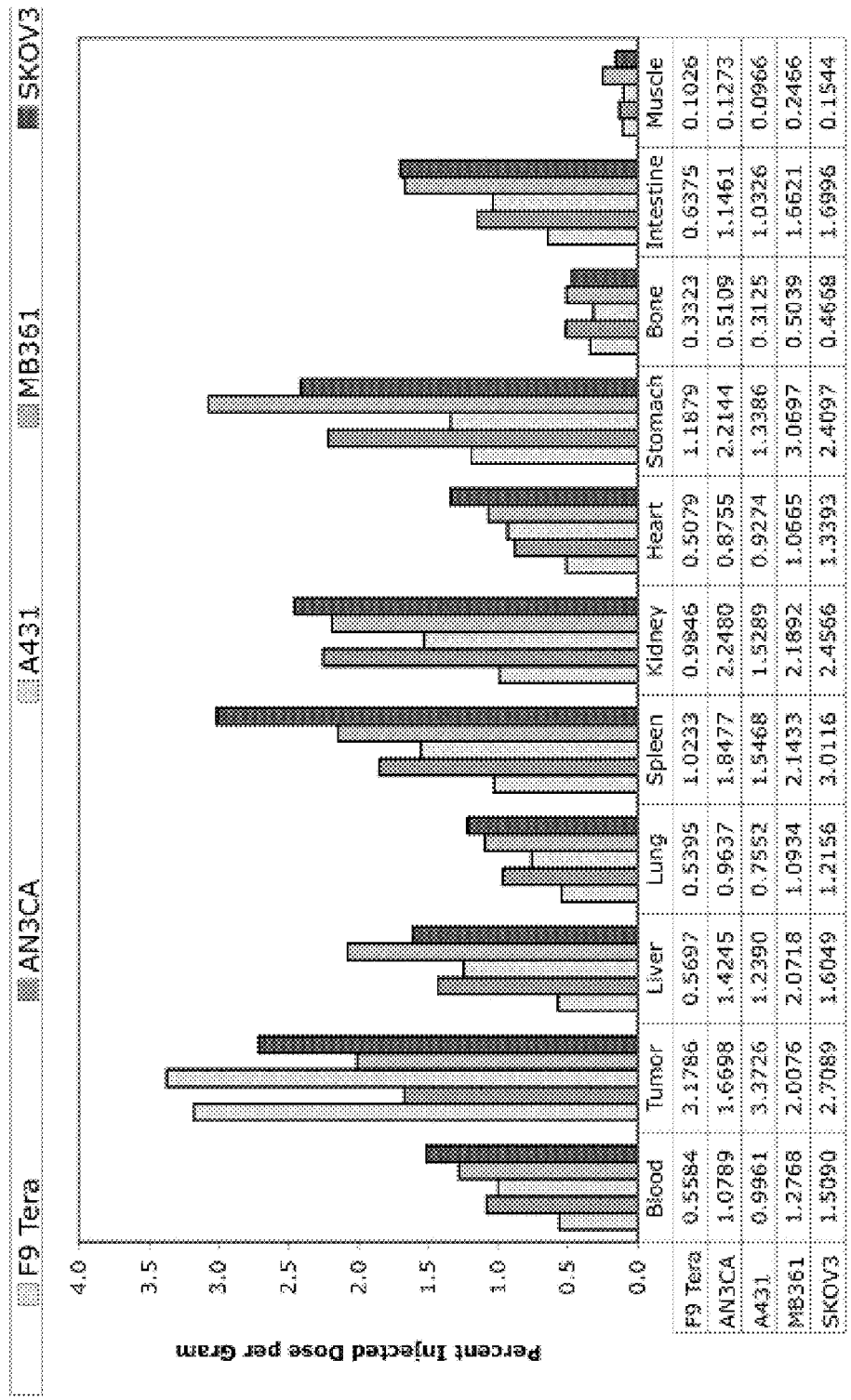
FIG. 2a shows biodistribution of $^{125}I$ labeled scFv#4 at 24 hours post-injection in SCID mice bearing various tumors.
Figure 2B:
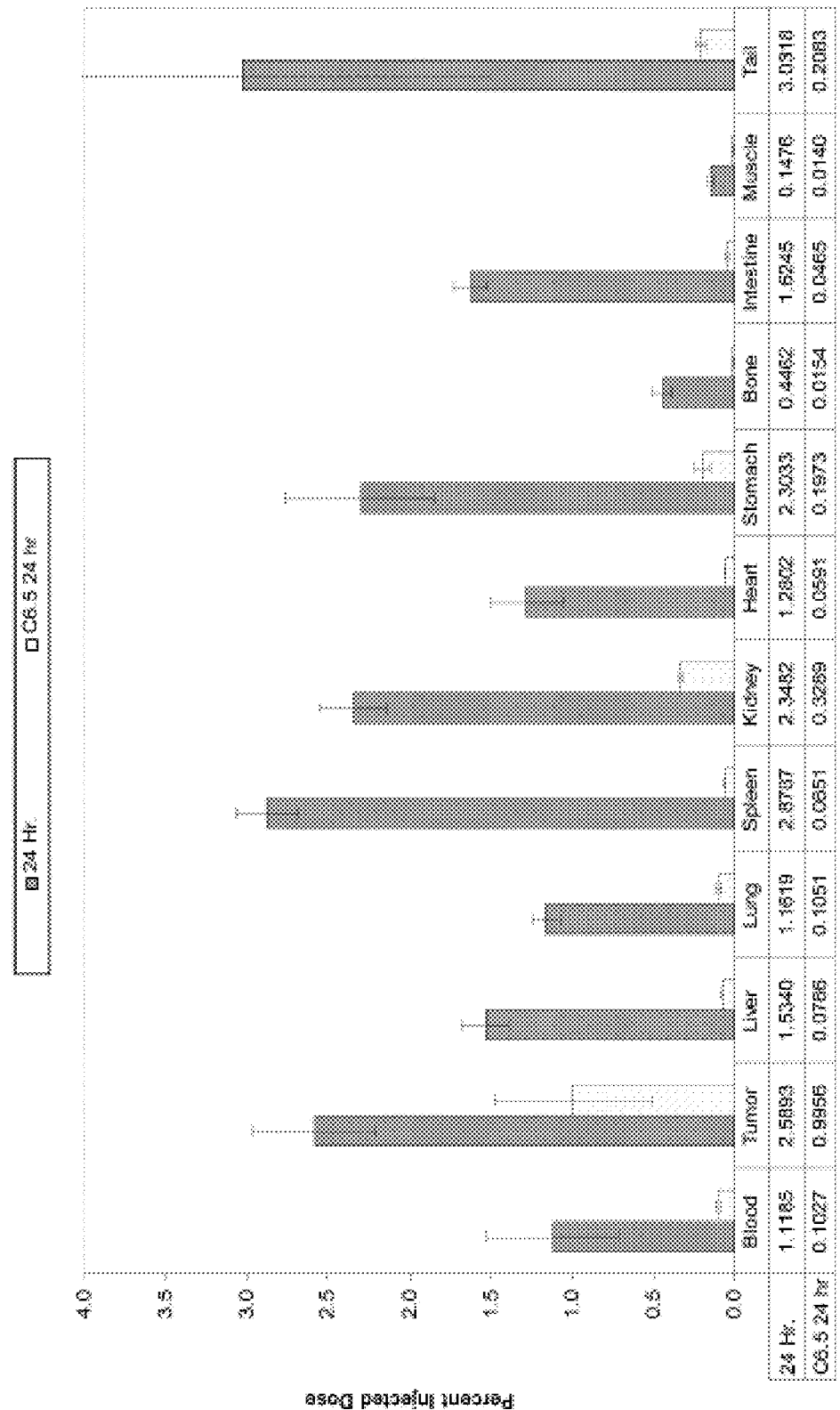
FIG. 2b shows biodistribution of $^{125}I$ labeled scFv#4 in SKOV3 cells.
Figure 2C:
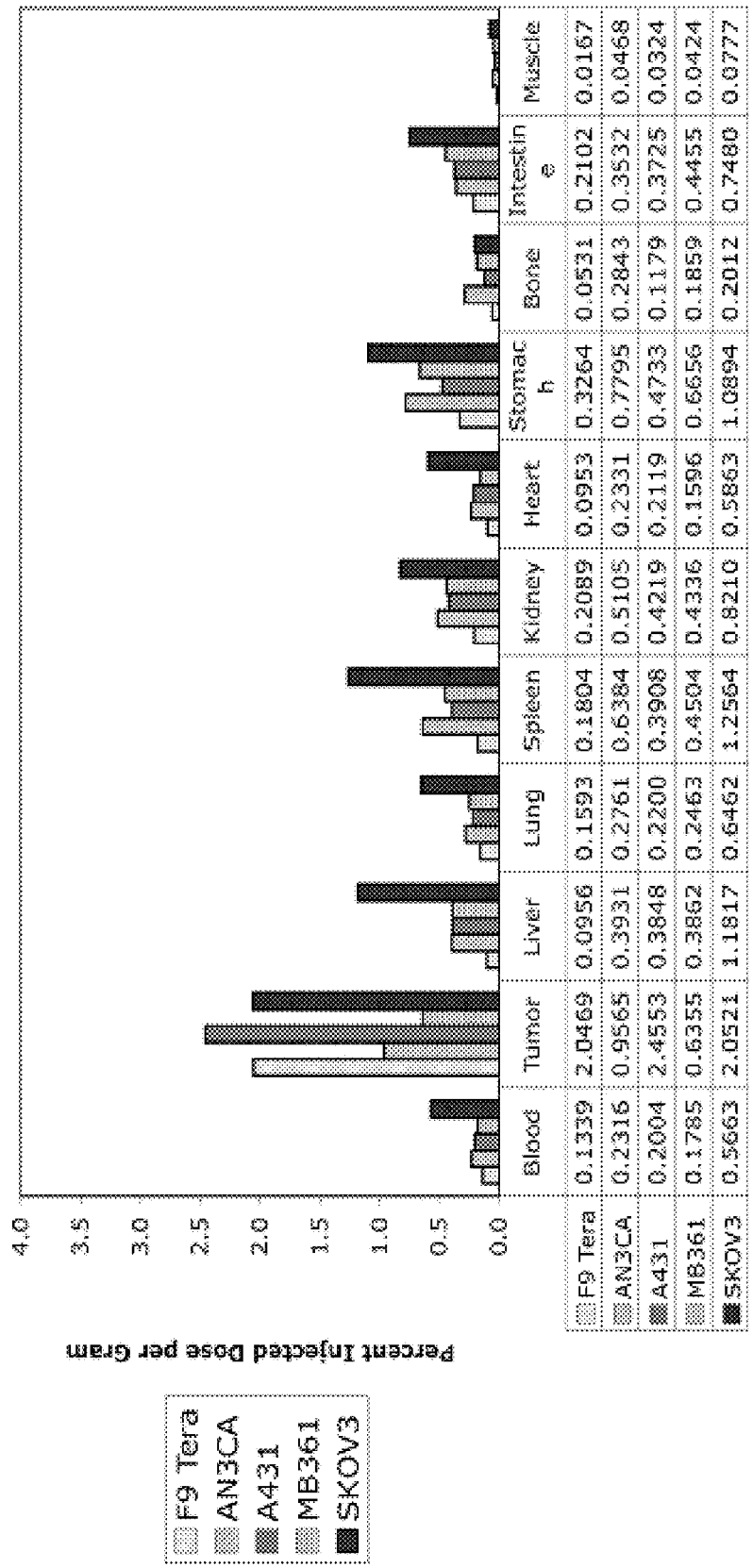
FIG. 2c shows biodistribution of $^{125}I$ labeled scFv#4 at 48 hours. For FIGS. 2a and 2c, in each group (e.g., blood, tumor, liver, etc.), the bars moving from left to right correspond to the following cell types: F9 Teratocarcinoma, AN3CA, A431, MB361, SKOV3.

The results demonstrate that antibody BB1 clearly binds to purified TEM7R extracellular domain in flow cytometry studies and cross reacts with human and mouse proteins (FIGS. 9 and 10). The scFv antibody construct against TEM7R is capable of tumor targeting in biodistribution experiments using five different cell lines (FIGS. 2a-c). Moreover, this scFv in positron emission tomography (PET) imaging exhibits excellent targeting and tumor specificity (FIG. 3). Immunohistochemistry (IHC) and immunofluorescence (IF) studies with the IgG1 confirms vascular targeting in A431 derived tumors (FIGS. 6 and 7) and in F9 derived tumors (FIG. 8). This antibody also appears to slow tumor growth as suggested by the experiments performed with Matrigel® experiments. In these experiments, tumors grown in the presence of the antibody BB1 and control bevacizumab (Avastin®) are much smaller than the control tumors (FIGS. 11-15).

Antibody-drug conjugates have been gaining popularity due to their potentially broad applicability. Here, an antibody is used to deliver a cytotoxic drug to a target that is overexpressed by tumors. These conjugates could enhance the anti-tumor activities of antibodies and improve the ratio of delivery of drug in the tumor vs. normal tissue. Internalization of the antibody would lead to the release of the toxic pay load inside the cells that express the target. In the F9 tumor cell line model presented herein, BB1 is internalized as shown in FIG. 16. Mouse xenografts experiments using an immunotoxin-conjugated antibody are planned.

The invention is not limited to the embodiments described and exemplified above, but is capable of variation and modification within the scope of the appended claims.

We claim:

1. An isolated antibody, comprising a heavy chain variable region having the amino acid sequence of SEQ ID NO: 9 and a light chain variable region, wherein the antibody specifically binds to an epitope on the extracellular domain of TEM7R.

2. The antibody of claim 1, wherein the light chain variable region comprises the amino acid sequence of SEQ ID NO: 10.

3. The antibody of claim 1, wherein the antibody is a monoclonal antibody.

4. The antibody of claim 1, wherein the antibody comprises a single chain Fv.

5. The antibody of claim 4, wherein the single chain Fv comprises the amino acid sequence of SEQ ID NO: 11.

6. The antibody of claim 1, wherein the antibody is a chimeric antibody.

7. The antibody of claim 1, wherein the antibody is conjugated to a chemotherapeutic agent.

8. The antibody of claim 1, wherein the antibody is conjugated to a detectable label.

9. The antibody of claim 1, wherein the TEM7R is human TEM7R.

10. The antibody of claim 1, wherein the TEM7R is mouse TEM7R.

11. A composition, comprising the antibody of claim 1 and a pharmaceutically acceptable carrier.

12. A composition, comprising the antibody of claim 7 and a pharmaceutically acceptable carrier.

13. An isolated antibody, comprising a. light chain variable region having the amino acid sequence of SEQ ID NO, 10and a heavy chain variable region, wherein the antibody specifically binds to an epitope on the extracellular domain of TEM7R.

14. The antibody of claim 13, wherein the heavy chain variable region comprises the amino acid sequence of SEQ ID NO: 9.

15. The antibody of claim 13, wherein the antibody is a monoclonal antibody.

16. The antibody of claim 13, wherein the antibody comprises a single chain Fv.

17. The antibody of claim 16, wherein the single chain Fv comprises the amino acid sequence of SEQ ID NO: 11.

18. The antibody of claim 13, wherein the antibody is a chimeric antibody.

19. The antibody of claim 13, wherein the antibody is conjugated to a chemotherapeutic agent.

20. The antibody of claim 13, wherein the antibody is conjugated to a detectable label.

21. The antibody of claim 13, wherein the TEM7R is human TEM7R.

22. The antibody of claim 13, wherein the TEM7R is mouse TEM7R.

23. A composition, comprising the antibody of claim 13 and a pharmaceutically acceptable carrier.

24. A composition, comprising the antibody of claim 20 and a pharmaceutically acceptable carrier.

* * * * *

UNITED STATES PATENT AND TRADEMARK OFFICE
CERTIFICATE OF CORRECTION

Page 1 of 1

PATENT NO. : 9,534,050 B2
APPLICATION NO. : 14/514493
DATED : January 3, 2017
INVENTOR(S) : Hossein Borghaei et al.

It is certified that error appears in the above-identified patent and that said Letters Patent is hereby corrected as shown below:

On the Title Page

Related U.S. Application Data should read:

(63) Continuation of application No. 13/697,024 filed on November 9, 2012, now Pat. No. 8,883,978, which is a 371 of application No. PCT/US2011/036124 filed on May 11, 2011.

Signed and Sealed this
Twenty-first Day of March, 2017

Michelle K. Lee
*Director of the United States Patent and Trademark Office*